(12) United States Patent
Emerson et al.

(10) Patent No.: US 12,230,363 B2
(45) Date of Patent: Feb. 18, 2025

(54) EFFICIENTLY CHARACTERIZING PROTEIN-PROTEIN INTERACTIONS

(71) Applicant: A-Alpha Bio, Seattle, WA (US)

(72) Inventors: Ryan Emerson, Seattle, WA (US); Randolph Lopez, Seattle, WA (US); David Younger, Seattle, WA (US)

(73) Assignee: A-Alpha Bio, Seattle, WA (US)

( * ) Notice: Subject to any disclaimer, the term of this patent is extended or adjusted under 35 U.S.C. 154(b) by 0 days.

(21) Appl. No.: 18/764,600

(22) Filed: Jul. 5, 2024

(65) Prior Publication Data

US 2024/0363194 A1   Oct. 31, 2024

Related U.S. Application Data

(63) Continuation of application No. PCT/US2023/037104, filed on Nov. 9, 2023.

(60) Provisional application No. 63/424,382, filed on Nov. 10, 2022.

(51) Int. Cl.
*G16B 35/20* (2019.01)
*C12N 15/10* (2006.01)
*G16B 15/30* (2019.01)

(52) U.S. Cl.
CPC ......... *G16B 15/30* (2019.02); *C12N 15/1037* (2013.01); *G16B 35/20* (2019.02)

(58) Field of Classification Search
None
See application file for complete search history.

(56) References Cited

U.S. PATENT DOCUMENTS

| | | |
|---|---|---|
| 10,988,759 B2 | 4/2021 | Baker et al. |
| 11,136,573 B2 | 10/2021 | Baker et al. |
| 11,474,111 B2 | 10/2022 | Younger et al. |
| 11,726,097 B2 | 8/2023 | Younger et al. |
| 11,820,970 B2 | 11/2023 | Baker et al. |
| 2003/0119056 A1 | 6/2003 | Ladner |
| 2008/0207467 A1 | 8/2008 | Moore et al. |
| 2010/0209414 A1 | 8/2010 | Schmidt et al. |
| 2017/0316147 A1 | 11/2017 | Gao et al. |
| 2022/0251543 A1 | 8/2022 | Younger et al. |

FOREIGN PATENT DOCUMENTS

| | | |
|---|---|---|
| WO | WO 2020/207944 | 10/2020 |
| WO | WO 2021/231013 | 11/2021 |
| WO | WO 2024/102448 | 5/2024 |

OTHER PUBLICATIONS

PCT International Search Report and Written Opinion in International Appln. No. PCT/US2023/037104, mailed on Apr. 12, 2024, 17 pages.

*Primary Examiner* — Christopher M Gross
(74) *Attorney, Agent, or Firm* — Fish & Richardson P.C.

(57) ABSTRACT

The present disclosure provides methods for improving libraries for screening protein-protein interactions (PPI) by excluding amino acid substitutions that are predicted to have a redundant or minimal effect on binding between protein binding partners.

18 Claims, 27 Drawing Sheets

FIG. 2C
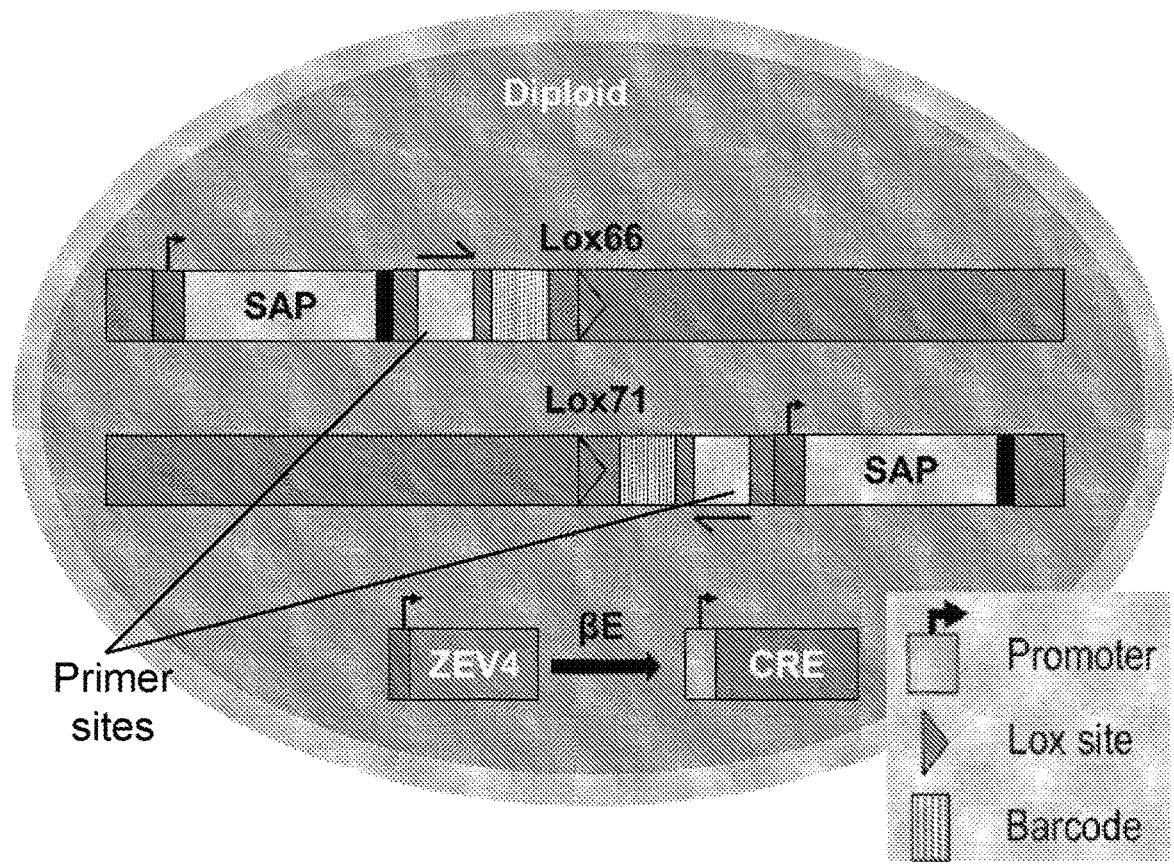
Following CRE translocation constructs are at same genomic target locus
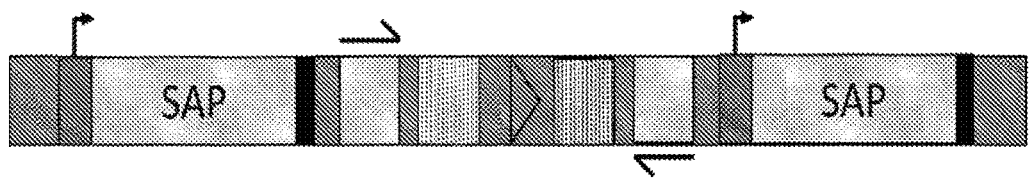
Amplify target DNA using primers to unique primer sites
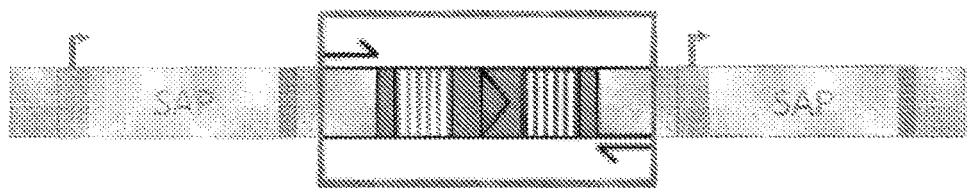

600

Start

↓

Provide a target library comprising a plurality of target polypeptide variants of a target protein
602

↓

Measure binding affinities between each target polypeptide variant of the target library and each of a plurality of binding polypeptides
604

↓

Cluster, based on the binding affinities, the binding polypeptides using a correlation distance metric and agglomerative hierarchical clustering to identify one or more groups of related binding profiles
606

↓

Apply feature selection to the target library to identify a subset of target polypeptide variants that distinguish binding profiles for binding to the target protein
608

↓

Provide a list of amino acid substitutions that affect protein-protein interactions from the subset of target polypeptide variants
610

*FIG. 6*

```
# Magic
%matplotlib inline

# Basic packages
import numpy as np
import pandas as pd
import re
import statistics

# Feature selection
from mlxtend.feature_selection import SequentialFeatureSelector as SFS
from eobox.ai import ffgs

# Cross-validation
from sklearn.model_selection import RepeatedStratifiedKFold
from sklearn.model_selection import cross_validate

# Multi-class classification algorithm
from sklearn.neighbors import KNeighborsClassifier

# Additional sklearn modules
from sklearn.model_selection import train_test_split

# Plotting
import matplotlib.pyplot as plt
import matplotlib.colors as mcolors
import matplotlib as mpl
from matplotlib.colors import ListedColormap
import scipy.cluster
from scipy.cluster import hierarchy
```

FIG. 14

```
# Rating results file
input_filename = 'TIGIT_TIGIT_Rating_Results.csv'

# Substring match defining binders to analyze
binder_string = 'TIGIT'

# Name of the SSM library target
SSM_name = 'TIGIT_22-132_A01-AGA2'

# The axis in which we have binders
binder_axis = 'mata_description'

# The axis in which we have a target SSM library
SSM_axis = 'matalpha_description'

# Predicted binding affinities, this should match the column header of the CSV file
pred_aff = 'pred_aff'

# Regular expressions to define wild-type (WT) comparator sequences and SSM library members
WT_regex = r'^([A-Z])[0-9]{1,3}\1'  # A letter, 1-3 numbers, and then "the same" letter, e.g. D46D
SSM_regex = r'^[A-Z][0-9]{1,3}[A-Z]'  # A letter, 1-3 numbers, and then another letter, e.g. D46Y

# Filtering threshold for epitope discovery
epi_thresh = 1.0

# Classification algorithm
mod = KNeighborsClassifier(n_neighbors=5)

# Cross-validation
cv = RepeatedStratifiedKFold(n_repeats=3, n_splits=5, random_state=0)
```

FIG. 15

```
# Input dataframe
df_import = pd.read_csv(input_filename, sep=',')

# Output dataframes
df_combined_epi = pd.DataFrame() # per site
df_combined_epi_mutation_x_site = pd.DataFrame() # Per mutation type

# Iterate through each binder
for binder in df_import[binder_axis].unique():
    if (binder_string in binder):
        binder_name = binder.strip()
        print('Working on ' + binder_name)

# Split binders into different dfs
        df_reduced = df_import[df_import[binder_axis] == binder].reset_index(drop=True)

# Subset each binder df to just those with the WT antigen
        df_WT = df_reduced[df_reduced[SSM_axis].str.contains(SSM_name)]
        # Calculate the mean affinity for all
        WT_aff = df_WT[pred_aff].mean()

# If WT or binder has really weak binding (>3)...skip
        if(np.isnan(WT_aff) or WT_aff > 3):
            print("Binding too weak, discarding binder.")
            continue

# Subset each binder df to all SSM mutations (non-WT)
        df_SSM = df_reduced[df_reduced[SSM_axis].str.contains(SSM_regex, regex=True)]
        # Impute NAs with an affinity 2 logs worse than WT
        df_SSM = df_SSM.copy()
        df_SSM.loc[:, pred_aff] = df_SSM[pred_aff].fillna(WT_aff + 2)
        # Calculate adjusted affinities by subtracting the WT affinity from the predicted affinity
        df_SSM.loc[:,'adj_aff'] = df_SSM[pred_aff] - WT_aff
```

FIG. 16A

```
# Pivot to mutation x site
df_SSM_mutation_x_site = df_SSM
df_SSM_mutation_x_site.loc[:,'abs_adj'] = np.absolute(df_SSM_mutation_x_site['adj_aff'])
df_SSM_mutation_x_site = pd.pivot_table(df_SSM_mutation_x_site, values='abs_adj', index=binder_axis, columns=SSM_axis)

# Get the average predicted and adjusted affinities for each antigen for each binder
df_SSM_avg = pd.pivot_table(data=df_SSM, values = [pred_aff,'adj_aff'], aggfunc=[np.mean], index=SSM_axis)

df_SSM = df_SSM_avg.reset_index()
df_SSM.columns = [SSM_axis,'adj_aff','pred_aff']
df_SSM_split = df_SSM[SSM_axis].str.split(r'([A-Z])([0-9]+)([A-Z])', expand=True)
df_SSM_split.columns = ['index', 'site', 'mutation', 'codon']
df_SSM.loc[:,'site'] = df_SSM_split['site']
df_SSM.loc[:,'mutation'] = df_SSM_split['mutation']
df_SSM_sites = df_SSM
# Order by site
df_SSM_sites.loc[:,'int_site'] = df_SSM_sites.site.astype(int)
df_SSM_sites.sort_values(by=['int_site', 'mutation'], ascending=True, inplace=True)

# Get the absolute value of the adjusted affinity
df_SSM_sites.loc[:,'abs_adj'] = np.absolute(df_SSM_sites['adj_aff'])
# Get the mean of the absolute values of the adjusted affinities at each site
df_reduced_sites = pd.pivot_table(data=df_SSM_sites, values='abs_adj', aggfunc=np.mean, index='int_site').reset_index()
# Add a column of binder names
df_reduced_sites.loc[:,'Ab'] = binder

# Save output
df_combined_epi = pd.concat([df_combined_epi, df_reduced_sites], ignore_index=True)
df_combined_epi_mutation_x_site = pd.concat([df_combined_epi_mutation_x_site, df_SSM_mutation_x_site], ignore_index=False)

display(df_combined_epi)
display(df_combined_epi_mutation_x_site)
```

FIG. 16B

```
class MyNormalize(mcolors.Normalize):
    def __call__(self, value, clip=None):
        # function to normalize any input between vmin and vmax linearly to [0,1]
        n = lambda x: (x-self.vmin)/(self.vmax-self.vmin)
        # nonlinear function between [0,1] and [0,1]
        f = lambda x: x**1.5
        return np.ma.masked_array(f(n(value)))
```

FIG. 17

```
df_matrix = pd.pivot_table(data=df_combined_epi, index='Ab', columns='int_site', values='abs_adj').reset_index()
df_matrix = df_matrix.set_index('Ab', drop=True)
df_matrix2 = df_matrix.div(df_matrix.mean(axis=1), axis=0)
df_matrix3 = df_matrix2.div(df_matrix2.mean(axis=0), axis=1)

# Keep only rows where the maximum value is greater than 1.0
df_matrix3S = df_matrix3[np.max(df_matrix3, axis=1) > epi_thresh]

fig, axs = plt.subplots(ncols=3, figsize=(18, 14), constrained_layout=False,
                       gridspec_kw={'width_ratios': [20, 100, 1], 'wspace':0.8})

cmap = ['#0121b4', '#008188', '#008080', '#f59e00', '#8f4164']
hierarchy.set_link_color_palette(cmap)

lnk = scipy.cluster.hierarchy.linkage(df_matrix3S, 'average', metric='correlation', optimal_ordering=True)
with plt.rc_context({'lines.linewidth':0.75}):
    dendro = scipy.cluster.hierarchy.dendrogram(lnk, get_leaves=True, ax=axs[0], orientation='left',
                                                labels=df_matrix3S.index, above_threshold_color='#ababab', color_threshold=.8)
leaves = dendro['leaves']

df_matrix5 = df_matrix3S.reset_index(drop=False)
df_matrix5 = df_matrix5.reindex(leaves)
df_matrix5 = df_matrix5.set_index('Ab', drop=True)

WT = df_import[df_import[SSM_axis].str.contains(WT_regex, regex=True)].dropna()
WT = WT.groupby(binder_axis).mean()

WT = WT.reindex(df_matrix5.index)
WT = WT[[pred_aff]]

# Return 100 different blue values between 0 and 0.8
blue_cmap = ListedColormap(mpl.cm.Blues(np.linspace(0, 0.8, 100)))
norm = MyNormalize(vmin=0.0, vmax=1)

ax2 = axs[1].imshow(df_matrix5[:,:-1], cmap=blue_cmap, aspect='auto', norm=norm)
ax3 = axs[2].imshow(WT[:,:-1], cmap='Reds', aspect='auto', norm=norm)
```

FIG. 18A

```
# Comment out for unlabeled WT affinities
#WT_flip = pd.DataFrame(WT.values[::-1])
#for y in range(WT_flip.shape[0]):
#    for x in range(WT_flip.shape[1]):
#        axs[2].text(x, y, '%.2f' % WT_flip.iloc[y, x],
#                    fontsize=2,
#                    rotation=90,
#                    horizontalalignment='center',
#                    verticalalignment='center')

for ax in axs:
    ax.set_xticks([])
    ax.spines[:].set_visible(False)

axs[1].set_xticks(np.arange(df_matrix5.shape[1]))
axs[1].set_xticklabels(df_matrix5.columns, rotation=90)
axs[1].tick_params(axis='x', labelsize=3)

# Comment out for unlabeled adjusted affinities
#df_matrix5_flip = pd.DataFrame(df_matrix5.values[::-1])
#for y in range(df_matrix5_flip.shape[0]):
#    for x in range(df_matrix5_flip.shape[1]):
#        axs[1].text(x, y, '%.2f' % df_matrix5_flip.iloc[y, x],
#                    fontsize=2,
#                    rotation=90,
#                    horizontalalignment='center',
#                    verticalalignment='center')

axs[1].grid(which='minor')

fig.set_facecolor('white')
```

FIG. 18B

```
fclust = hierarchy.fcluster(lnk, t=.2, criterion='distance')
df_fclust = pd.DataFrame({'binder': df_matrix35.index, 'cluster':fclust})

# Remove clusters with 1 binder
df_fclust_final = df_fclust[df_fclust.groupby('cluster').cluster.transform('count') > 1]
```

```
feature_names = df_combined_epi_mutation_x_site_final.columns
```

FIG. 21A

```
X = df_combined_epi_mutation_x_site_final.iloc[:,:].values
```

FIG. 21B

```
y = np.array(df_fclust_final['cluster'])
```

FIG. 21C

```
# Remove site number, get rid of 'ab' and 'target' columns
groups = df_combined_epi_mutation_x_site_final.columns.str.replace(r'[0-9]{1,3}', '', regex=True)

# Get a list of indices that will be applied to the groups
indices = np.arange(0, len(groups), 1, dtype=int)

# Turn groups and indices into a dataframe
group_df = pd.DataFrame({'groups':groups, 'indices':indices})

# List all of the indices for each group
group_df2 = group_df.groupby(by='groups')['indices'].apply(list)

# Turn back into a dataframe
group_df3 = group_df2.to_frame()
# Make 'groups' a column instead of an index
group_df3.reset_index(inplace=True)
# Turn the indices into a new column, will turn into the group numbers for each group
group_df3.reset_index(inplace=True)
group_df3.rename(columns={'index': 'group_num'}, inplace=True)
group_df3.to_csv('group_df.csv', header=True, index=False)

# Turn numbered groups and their indices into a dictionary
fgroups_dict = dict(zip(group_df3.group_num, group_df3.indices))

# Make an array of zeros equal to the number of columns in X_train
fgroups = np.zeros(X.shape[1], dtype=int)

# Replace zeros in the above array with group numbers
for group, feature_indices in fgroups_dict.items():
    fgroups[np.array(feature_indices)] = group
```

FIG. 21D

```
# Generate a list of 100 random states for splitting
#random_list = []

#for i in range(0,100):
#    n = random.randint(1, 1000000)
#    random_list.append(n)

#print(random_list)

# list of 100 states copied from random generator above for reproducibility
random_list = [800888, 83178, 157285, 690467, 600060, 467888, 106333, 988644, 884740, 811978, 288758, 344115,
               185884, 35528, 787681, 175996, 62810, 567836, 114938, 718036, 428788, 387661, 258484, 924582,
               134864, 472886, 878188, 878677, 517909, 881589, 438063, 788444, 240615, 385828, 854837, 557815,
               446882, 486137, 756654, 19828, 996885, 278809, 462805, 685986, 364551, 115159, 838889, 172881,
               822889, 816381, 680225, 6418, 741814, 685588, 245112, 658921, 215753, 453488, 111875, 884789,
               54846, 567034, 658781, 609633, 988788, 724284, 307308, 899713, 628788, 218263, 259986, 789986,
               755225, 295664, 444446, 878796, 478722, 995311, 888585, 735289, 174844, 816888, 168888, 238986,
               582253, 820585, 369392, 141401, 542476, 989917, 869948, 8881, 979390, 866689, 984291, 895631,
               879782, 850899, 742827, 378947]
```

FIG. 22A

```
X_train_list = []
X_test_list = []
y_train_list = []
y_test_list = []

for i in random_list:
    X_train, X_test, y_train, y_test = train_test_split(X, y,
                                                        test_size = 0.2,
                                                        random_state=i,
                                                        stratify=y)
    X_train_list.append(X_train)
    X_test_list.append(X_test)
    y_train_list.append(y_train)
    y_test_list.append(y_test)
```

FIG. 22B

```
def FFGS(X_train, y_train, X_test, y_test, cv):
    global fsel
    # Forward feature group selection (FFGS)
    fsel = ffgs.ForwardFeatureGroupSelection(mod,
                                             k_features=(1, X.shape[1]),
                                             scoring='accuracy',
                                             verbose=0,
                                             cv=cv,
                                             n_jobs=10)

# Fit the training data
    fsel = fsel.fit(X_train, y_train, custom_feature_names=feature_names, fgroups=fgroups)

# Features
    global best_features
    best_features = np.array(fsel.k_feature_names_)
    print('Best feature combination: ', best_features)

# Groups
    global best_groups
    best_groups = [re.sub(r'[0-9]{1,3}', '', feature) for feature in fsel.k_feature_names_]
    best_groups = np.array(best_groups)
    best_groups = np.unique(best_groups)
    print('Best groups combination: ', best_groups)

# Number of features
    global best_features_num
    best_features_num = len(fsel.k_feature_names_)
    print('Number of features (k): ', best_features_num)

# Number of Groups
    global best_groups_num
    best_groups_num = len(best_groups)
    print('Number of groups: ', best_groups_num)

# Train ACC
    global acc_train
    acc_train = fsel.k_score_ * 100
    print('Training set ACC: %.2f %%:' % acc_train)

# Make new predictions using the selected feature subset and the test data
    # Generate the new subsets based on the selected features
    # Note that the transform call is equivalent to
    # X_train[:, sfs_1.k_feature_idx_]
    X_train_transformed_fsel = fsel.transform(X_train)
    X_test_transformed_fsel = fsel.transform(X_test)

# Fit the estimator using the new feature subset and make a prediction on the test data
    mod.fit(X_train_transformed_fsel, y_train)
    y_pred = mod.predict(X_test_transformed_fsel)

# Test ACC
    global acc_test
    acc_test = (float((y_test == y_pred).sum()) / y_pred.shape[0])*100
    print('Test set ACC: %.2f %%' % (acc_test))
    print('\n')
```

```
# List of all random states
best_groups_num_states = []
for i in random_list:
    x = "best_groups_num_" + str(i)
    best_groups_num_states.append(x)

# Combine lists of features for each state
best_groups_num = []
for i in best_groups_num_states:
    best_groups_num.append(eval(i))

# Mean
avg_best_groups_num = statistics.mean(best_groups_num)

# SD
sd_best_groups_num = statistics.stdev(best_groups_num)

print("Average best number of groups: %.0f" % avg_best_groups_num, u"\u00B1 %.0f" % sd_best_groups_num)
Average best number of groups: 16 ± 23
```

FIG. 25A

```
# List of all random states
acc_train_states = []
for i in random_list:
    x = "acc_train_" + str(i)
    acc_train_states.append(x)

# Combine lists of features for each state
acc_train = []
for i in acc_train_states:
    acc_train.append(eval(i))

# Mean
avg_acc_train = statistics.mean(acc_train)

# SD
sd_acc_train = statistics.stdev(acc_train)

print("Average training ACC: %.2f %%" % avg_acc_train, u"\u00B1 %.2f %%" % sd_acc_train)
Average training ACC: 99.81 % ± 0.42 %
```

```
feature_names_sub = df_sub.columns
```

*FIG. 27A*

```
x_sub = df_sub.iloc[:,:].values
```

*FIG. 27B*

```
y_sub = df_fclust_final['cluster']
```

*FIG. 27C*

```
# fit the estimator
mod.fit(x_sub, y_sub)

# make new predictions
y_pred = mod.predict(x_sub)
print("Binder classification results: ", y_pred)

# Test accuracy
acc_test = float((y_sub == y_pred).sum()) / y_pred.shape[0]
print("Test set ACC: %.2f %%" % (acc_test * 100))

Binder classification results:  [1 4 1 4 4 4 4 5 1 5 4 4 5 3 4 5 9 4 5 5 3 3 3 4 4 3 5 5 3 4 3 4 5 5 3 5
 4 5 6 1 4 6 4 4 5 1 5 5 4 6 5 4 6 1 3 5 6 5 5 6 1 1 1 4 5 4 5 3 5 3 9 4 3
 6 5 5 3 3 5 4 3 6 3 3 4 4 4 3 4 4 3 1 6 5 3 1 3 4 4 3 4 3 5 3 4 3 3 4 6 3
 4 6 3 1 1 4 4 6]
Test set ACC: 100.00 %
```

*FIG. 27D*

```
cross_validate(mod, X_sub, y_sub, scoring='accuracy', cv=5, return_train_score=True)

{'fit_time': array([0.00060749, 0.00057721, 0.00054802, 0.00053   , 0.00054802]),
 'score_time': array([0.00241637, 0.00189137, 0.0018723 , 0.00187945, 0.00183678]),
 'test_score': array([0.95833333, 1.        , 1.        , 1.        , 1.        ]),
 'train_score': array([1.        , 1.        , 0.98947368, 1.        , 1.        ])}
```

*FIG. 27E*

EFFICIENTLY CHARACTERIZING PROTEIN-PROTEIN INTERACTIONS

CROSS-REFERENCE TO RELATED APPLICATIONS

This application is a continuation of International Application No. PCT/US2023/037104, filed Nov. 9, 2023 (published as WO 2024/102448 on May 16, 2024), which claims the benefit of U.S. Provisional Patent Application No. 63/424,382, filed on Nov. 10, 2022, each of which are incorporated herein by reference in their entirety.

TECHNICAL FIELD

This document relates to methods of efficiently characterizing the binding sites that mediate protein-protein interactions.

BACKGROUND

Identification of binding sites that comprise a particular protein-protein interaction (PPI) is important for characterizing the PPI, e.g., the identification of paratope and epitope residues when studying an antibody-antigen interaction. Traditional methods are cumbersome, low-throughput, laborious, and expensive. Higher throughput is of substantial interest in the field, with the eventual goal of an assay capable of identifying specific binding interfaces at roughly the same scale as candidate binders are identified from natural or synthetic immunization experiments (i.e., hundreds to hundreds of thousands at a time).

Site-saturation mutagenesis (SSM) can be used to screen PPIs in a high-throughput library-by-library manner. For example, epitope mapping can be done by a variety of methods including mass spectrometry, surface plasmon resonance (SPR) using a plate-based peptide assay, one binder at a time methods, or mutational scanning. Previous methods using yeast synthetic agglutination include, for example, U.S. Patent Nos. 10,988,759 and 11,136,573, which are hereby incorporated by reference in their entireties. However, further increases in the multiplicity and throughput of the process of screening PPIs remain relevant.

SUMMARY

The present disclosure is based, at least in part, on the discovery that for a screen of protein-protein interactions (PPIs), for example a library-by-library screen of interactions between protein binding partners, reducing the size of the respective libraries of protein binding partner variants to exclude amino acid substitutions that are predicted to have a redundant or minimal effect on binding—and thus provide little independent information about the binding interface—can increase the number of protein binding partners that can be interrogated by a given screening platform. In addition, reducing library size can increase the accuracy of PPI characterization for a given number of protein binding partners by increasing resolution. The present disclosure provides methods of predicting which amino acid substitutions at a given amino acid location in a protein are most likely to result in an informative difference in binding when assessing a particular PPI, allowing for a ten-fold or more reduction in required library size and a corresponding increase in screening capacity and PPI characterization accuracy. The present disclosure also provides lists of the most informative amino acid substitutions that are predicted by the methods disclosed herein to most significantly affect the interaction of any two protein binding partners.

In one aspect, the present disclosure provides methods of identifying amino acid substitutions that affect protein-protein interactions (PPIs). The methods include providing a target library comprising a plurality of target polypeptide variants of a parental target protein; measuring binding affinities between each target polypeptide variant of the target library and each of a plurality of binding polypeptides; clustering, based on the binding affinities, the binding polypeptides to identify one or more groups of related binding profiles of the binding polypeptides; applying a feature selection algorithm to the target library to identify a subset of target polypeptide variants of the parental target protein comprising amino acid substitutions that distinguish the one or more identified groups of related binding profiles from each other for binding to the target protein; and providing a list of amino acid substitutions that affect PPIs from the subset of target polypeptide variants.

In some embodiments, the clustering is performed using a correlation distance metric. In some embodiments, the clustering is performed using agglomerative hierarchical clustering. In certain embodiments, the feature selection algorithm is a forward feature group selection (FFGS) algorithm. In some embodiments, the subset of target polypeptide variants of the target protein is 2-fold, 3-fold, 4-fold, 5-fold, 6-fold, 7-fold, 8-fold, 9-fold, or 10-fold smaller than the plurality of target polypeptide variants of the target protein.

In some embodiments, the affinities are measured using yeast surface display of the target polypeptide variants and the binding polypeptides. In some embodiments, the affinities are measured using synthetic yeast agglutination. In some embodiments, the target polypeptide variants are antigens. In some embodiments, the binding polypeptides are antibodies. In certain embodiments, applying FFGS includes providing a plurality of feature groups, in which each feature group includes target polypeptide variants sharing the same wild-type to mutant amino acid residue substitution at each position of the parental protein amino acid residue.

In another aspect, the disclosure provides methods of reducing the mutation space of a protein-protein interaction (PPI) screening platform. The methods include providing a target library comprising one or more target polypeptide variants of each of two or more different parental target proteins; measuring binding affinities between each target polypeptide variant of each parental target protein and each of a plurality of binding polypeptides; clustering, based on the binding affinities, the binding polypeptides using a correlation distance metric and agglomerative hierarchical clustering to identify one or more groups of related binding profiles of the binding polypeptides; applying a feature selection algorithm to the target library to identify a subset of target polypeptide variants of the one or more target proteins comprising amino acid substitutions that distinguish the one or more groups of related binding profiles from each other for binding to the target protein; and providing a list of amino acid substitutions that affect PPI, thereby reducing the mutation space of a PPI screening platform.

In some embodiments, the subset of target polypeptide variants of the one or more target parental proteins is 2-fold, 3-fold, 4-fold, 5-fold, 6-fold, 7-fold, 8-fold, 9-fold, or 10-fold smaller than the target library. In some embodiments, the feature selection algorithm is a forward feature group selection (FFGS) algorithm. In some embodiments, the affinities are measured using yeast surface display of the target polypeptide variants and the binding polypeptides. In some embodiments, the affinities are measured using synthetic yeast agglutination. In certain embodiments, the target polypeptide variants are antigens. In some embodiments, the binding polypeptides are antibodies. In some embodiments, applying FFGS includes providing a plurality of feature groups, in which each feature group includes target polypeptide variants sharing the same wild-type to mutant amino acid substitution.

In another aspect, the present disclosure provides compositions including one or more libraries of polypeptide variants of a parental target protein. In one aspect, the library can include a first set of polypeptide variants in which every A amino acid residue of the parental target protein has been mutated to a T amino acid residue, a second set of polypeptide variants in which every D amino acid residue of the parental target protein has been mutated to a V amino acid residue, a third set of polypeptide variants in which every E amino acid residue of the parental target protein has been mutated to a K amino acid residue, a fourth set of polypeptide variants in which every F amino acid residue of the parental target protein has been mutated to a P amino acid residue, a fifth set of polypeptide variants in which every G amino acid residue of the parental target protein has been mutated to an N amino acid residue, a sixth set of polypeptide variants in which every H amino acid residue of the parental target protein has been mutated to a P amino acid residue, a seventh set of polypeptide variants in which every I amino acid residue of the parental target protein has been mutated to an E amino acid residue, an eighth set of polypeptide variants in which every K amino acid residue of the parental target protein has been mutated to an E amino acid residue, a ninth set of polypeptide variants in which every L amino acid residue of the parental target protein has been mutated to an H amino acid residue, a tenth set of polypeptide variants in which every M amino acid residue of the parental target protein has been mutated to a W amino acid residue, an eleventh set of polypeptide variants in which every N amino acid residue of the parental target protein has been mutated to an L amino acid residue, a twelfth set of polypeptide variants in which every P amino acid residue of the parental target protein has been mutated to a Q amino acid residue, a thirteenth set of polypeptide variants in which every Q amino acid residue of the parental target protein has been mutated to a G amino acid residue, a fourteenth set of polypeptide variants in which every R amino acid residue of the parental target protein has been mutated to a K amino acid residue, a fifteenth set of polypeptide variants in which every S amino acid residue of the parental target protein has been mutated to an H amino acid residue, a sixteenth set of polypeptide variants in which every T amino acid residue of the parental target protein has been mutated to an R amino acid residue, a seventeenth set of polypeptide variants in which every V amino acid residue of the parental target protein has been mutated to a G amino acid residue, an eighteenth set of polypeptide variants in which every W amino acid residue of the parental target protein has been mutated to an N amino acid residue, and a nineteenth set of polypeptide variants in which every Y amino acid residue of the parental target protein has been mutated to an A amino acid residue.

In another aspect, the present disclosure provides compositions including one or more libraries of polypeptide variants of a parental target protein. In one aspect, the library can include at least 2, 3, 4, 5, 6, 7, 8, 9, 10, 11, 12, 13, 14, 15, 16, 17, 18, or 19 of the following sets of polypeptide variants: a first set of polypeptide variants in which every A amino acid residue of the parental target protein has been mutated to a T amino acid residue, a second set of polypeptide variants in which every D amino acid residue of the parental target protein has been mutated to a V amino acid residue, a third set of polypeptide variants in which every E amino acid residue of the parental target protein has been mutated to a K amino acid residue, a fourth set of polypeptide variants in which every F amino acid residue of the parental target protein has been mutated to a P amino acid residue, a fifth set of polypeptide variants in which every G amino acid residue of the parental target protein has been mutated to an N amino acid residue, a sixth set of polypeptide variants in which every H amino acid residue of the parental target protein has been mutated to a P amino acid residue, a seventh set of polypeptide variants in which every I amino acid residue of the parental target protein has been mutated to an E amino acid residue, an eighth set of polypeptide variants in which every K amino acid residue of the parental target protein has been mutated to an E amino acid residue, a ninth set of polypeptide variants in which every L amino acid residue of the parental target protein has been mutated to an H amino acid residue, a tenth set of polypeptide variants in which every M amino acid residue of the parental target protein has been mutated to a W amino acid residue, an eleventh set of polypeptide variants in which every N amino acid residue of the parental target protein has been mutated to an L amino acid residue, a twelfth set of polypeptide variants in which every P amino acid residue of the parental target protein has been mutated to a Q amino acid residue, a thirteenth set of polypeptide variants in which every Q amino acid residue of the parental target protein has been mutated to a G amino acid residue, a fourteenth set of polypeptide variants in which every R amino acid residue of the parental target protein has been mutated to a K amino acid residue, a fifteenth set of polypeptide variants in which every S amino acid residue of the parental target protein has been mutated to an H amino acid residue, a sixteenth set of polypeptide variants in which every T amino acid residue of the parental target protein has been mutated to an R amino acid residue, a seventeenth set of polypeptide variants in which every V amino acid residue of the parental target protein has been mutated to a G amino acid residue, an eighteenth set of polypeptide variants in which every W amino acid residue of the parental target protein has been mutated to an N amino acid residue, and a nineteenth set of polypeptide variants in which every Y amino acid residue of the parental target protein has been mutated to an A amino acid residue.

In another aspect, the present disclosure provides compositions including one or more libraries of polypeptide variants of a parental target protein, in which for each polypeptide variant of the library, every G amino acid residue of the parental target protein has been mutated to an N amino acid residue, a Y amino acid residue, or an L amino acid residue. In some embodiments, the composition includes a library of polypeptide variants of the parental target protein, in which for each polypeptide variant of the library, every G amino acid residue of the parental target protein has been mutated to an N amino acid residue. In some embodiments, the composition includes a library of polypeptide variants of the parental target protein, wherein for each polypeptide variant of the library, every G amino acid residue of the parental target protein has been mutated to a Y amino acid residue. In certain embodiments, the composition includes a library of polypeptide variants of the parental target protein, wherein for each polypeptide variant of the library, every G amino acid residue of the parental target protein has been mutated to an L amino acid residue.

In another aspect, the present disclosure provides a library of polypeptide variants of a parental target protein, in which for each polypeptide variant of the library, every A amino acid residue in the polypeptide has been mutated to a T amino acid residue, an I amino acid residue, an S amino acid residue, an L amino acid residue, or a D amino acid residue. In some embodiments, the composition includes a library of polypeptide variants of the parental target protein, wherein for each polypeptide variant of the library, every A amino acid residue of the parental target protein has been mutated to a T amino acid residue. In some embodiments, the composition includes a library of polypeptide variants of the parental target protein, wherein for each polypeptide variant of the library, every A amino acid residue of the parental target protein has been mutated to an I amino acid residue. In some embodiments, the composition includes a library of polypeptide variants of the parental target protein, wherein for each polypeptide variant of the library, every A amino acid residue of the parental target protein has been mutated to an S amino acid residue. In some embodiments, the composition includes a library of polypeptide variants of the parental target protein, wherein for each polypeptide variant of the library, every A amino acid residue of the parental target protein has been mutated to an L amino acid residue. In some embodiments, the composition includes a library of polypeptide variants of the parental target protein, wherein for each polypeptide variant of the library, every A amino acid residue of the parental target protein has been mutated to a D amino acid residue.

In another aspect, the present disclosure provides a library of polypeptide variants of a parental target protein, in which for each polypeptide variant of the library, every F amino acid residue of the parental target protein has been mutated to an I amino acid residue or a P amino acid residue. In some embodiments, the composition includes a library of polypeptide variants of the parental target protein, wherein for each polypeptide variant of the library, every F amino acid residue of the parental target protein has been mutated to an I amino acid residue. In some embodiments, the composition includes a library of polypeptide variants of the parental target protein, wherein for each polypeptide variant of the library, every F amino acid residue of the parental target protein has been mutated to a P amino acid residue. In some embodiments, the composition includes a library of polypeptide variants of the parental target protein, wherein for each polypeptide variant of the library, every L amino acid residue of the parental target protein has been mutated to an H amino acid residue.

In another aspect, the present disclosure provides computer-implemented methods for identifying amino acid substitutions that affect protein-protein interactions (PPIs). The methods include receiving, by a computing device including a processor programmed to execute software instructions within a memory, a set of protein-protein interaction measurements comprising pair-wise measurements of binding affinities between each target polypeptide variant of a library of target polypeptide variants and each binding polypeptide variant of a library of binding polypeptide variants; applying a machine learning algorithm to generate a classification model used in a classification scheme, wherein the machine learning algorithm has been trained using a stratified train-test split of the set of protein-protein interaction measurements comprising pair-wise measurements; applying, by the computing device, the classification scheme to rank the set of protein-protein interaction measurements; identifying, based on the ranking, a subset of target polypeptide variants of a parental target protein comprising amino acid substitutions that distinguish groups of related binding profiles from each other for binding to the parental target protein; and generating, by the computing device, a list of amino acid substitutions that affect PPIs from the subset of target polypeptide variants.

In some embodiments, the machine learning algorithm includes feature selection. In some embodiments, the feature selection includes forward feature group selection (FFGS). In some embodiments, the list of amino acid substitutions is a ranked list based on relevance of information provided by each amino acid substitution.

As used herein, "affinity" is the strength of a binding interaction between a single biomolecule to its ligand or binding partner. Affinity is usually measured and described using the equilibrium dissociation constant, $K_D$. The lower the $K_D$ value, the greater the affinity between the protein and its binding partner. Affinity may be affected by hydrogen bonding, electrostatic interactions, hydrophobic forces, and/or Van der Waals forces between the binding partners, or by the presence of other molecules, e.g., binding agonists or antagonists.

In some implementations, affinity is described using arbitrary units, wherein a certain binding affinity within an assay, for example the binding affinity between two wild-type protein binding partners or the wild-type species of a first protein binding partner and the wild-type species of a second protein binding partner, is set to an arbitrary unit of 1.0 and binding affinities for other pairs of protein binding partners, for example mutant species of a first protein binding partner and mutant species of a second protein binding partner, are measured relative to the arbitrary unit.

As used herein, "protein-protein interaction" or "PPI" refers to physical contacts of high specificity established between two or more proteins as a result of biochemical events driven by electrostatic forces including the hydrophobic effect. These physical contacts include molecular associations between chains that occur in a cell or in a living organism in a specific biomolecular context. In some embodiments, the protein-protein interactions are strong enough to replace the function of the native sexual agglutination proteins. For example, it is possible to couple mating efficiency to the interaction strength of a particular protein-protein interaction. In certain embodiments, the assay can characterize or determine protein-protein interactions between synthetic adhesion proteins (SAPs).

As used herein, a "synthetic adhesion protein" refers to any protein or polypeptide engineered to be expressed and assayed for binding to or interacting with any other any protein or polypeptide. The proteins can be exogenously expressed. Synthetic adhesion proteins are not associated with the adhesion required for agglutination as natively performed by naturally occurring sexual agglutination proteins. In certain embodiments, the synthetic adhesion proteins have interactions that are sufficiently strong to allow agglutination in yeast where the native sexual agglutination proteins are engineered not to be natively expressed.

As used herein, "alanine scan" refers to a mutagenesis technique used in protein engineering and molecular biology, wherein a specific type of amino acid is substituted with alanine at one or more positions in a polypeptide where the specific type of amino acid is located in the polypeptide. An alanine scan may be performed for one residue, several residues, or for residues at every position in the protein. The result is a library of mutant proteins representing mutations to alanine at one, several, or every amino acid position in a polypeptide. Other "amino acid scans" can also be used—for example, a "valine scan" or "leucine scan," in which amino acids are substituted with valine or leucine, respectively, at one or more positions in the polypeptide.

As used herein, a "target protein" is one polypeptide of a pair of polypeptide binding partners. A target protein interacts with a binding polypeptide. For example, for an interaction between an antibody and an antigen, the antigen is the target protein and the antibody is the binding polypeptide. As used herein, "target polypeptide variants" refers to a plurality of target proteins comprising a diversity of amino acid substitutions. A target protein variant can include one or more amino acid substitutions, relative to the parental target protein sequence, at one or more positions of the parental target protein's polypeptide sequence.

As used herein, "clustering" refers to a process of organizing objects or digital representations of objects, e.g., target polypeptide variants or digital representations thereof, of a parental target protein, into groups whose members are similar in some way. A "cluster" is therefore a group of objects, e.g., target polypeptide variants or digital representations, which are similar with respect to an attribute, e.g., a polypeptide binding site, and are dissimilar from objects belonging to other clusters.

As used herein, "feature selection" refers to a process of selecting a subset of one or more relevant features, e.g., a set of one or more amino acid substitutions, for use in model construction. The basis of feature selection techniques is that the data can contain certain features that are either redundant or irrelevant, and can thus be removed without incurring a significant loss of information. Redundant and irrelevant are two distinct notions, since one relevant feature may be redundant in the presence of another relevant feature with which it is strongly correlated.

As used herein, "forward feature group selection" (FFGS) refers to a feature selection method using an iterative approach beginning with an empty set of features and then adding a feature that best improves the model after each iteration. The stopping criterion is when the addition of a new variable does not improve the performance of the model. The FFGS process begins by evaluating all feature subsets that consist of only one input variable. The process selects the most informative single feature with respect to a designated scoring function; then, creates a model with that single most informative feature and each other feature and selects the most informative 2-feature model, and so on in that fashion.

As used herein, "related binding profiles" means, for a plurality of polypeptide variants, each variant, e.g., in a cluster, has a similar profile with respect to the difference in polypeptide binding affinity compared to an unmutated or "wild-type" sequence polypeptide binding partner, across a mutagenic library of the polypeptide binding partner.

As used herein, "mutation space" means the size of a library of polypeptide variants. For example, a library of polypeptide variants comprising a site saturation mutagenesis scan wherein every position of the polypeptide has been mutated to every possible amino acid would represent a larger mutation space than a library of polypeptide variants wherein all alanines are mutated to lysines.

As used herein, a "parental protein" or "parental target protein" means a protein or target protein from which variant polypeptide sequences are derived by introducing amino acid substitutions.

As used herein, "a polypeptide variant" or "variant polypeptide" means any polypeptide sequence comprising one or more amino acid substitutions relative to a reference amino acid sequence or a parental protein amino acid sequence, e.g., parental target protein amino acid sequence. For example, an "antibody variant" is an antibody sequence comprising one or more amino acid substitutions relative to the original polypeptide sequence of the antibody. In the context of the present disclosure, polypeptide variants comprise user-designated variants, produced by, for example, site-saturation mutagenesis (SSM) methods.

As used herein, a "library" refers to a plurality of variants of a biomolecule. For example for a plurality of polypeptide variants, each variant comprises one or more amino acid substitutions, relative to the parental protein sequence, at one or more amino acid positions of the protein sequence. A library can include a plurality of variants of a single protein, or a plurality of variants of two or more different parental proteins.

As used herein, a "binding polypeptide" or "binder" is one polypeptide of a pair of polypeptide binding partners. A binding polypeptide interacts with a target protein. For example, for an interaction between an antibody and an antigen, the antibody is the binding polypeptide and the antigen is the target protein.

As used herein, a "paratope" is a part of an antibody that specifically recognizes and binds to the antibody's corresponding antigen. A paratope is also known as an antigen-binding site. The amino acids comprising a paratope may be a continuous sequence of amino acid residues within the polypeptide chain of the antibody structure or may be discontinuous amino acid residues that confer conformational specificity upon the three-dimensional structure of the antibody structure.

As used herein, "paratope mapping" is a process of experimentally identifying and characterizing the composition of a paratope within an antibody protein structure. Paratope mapping can be used to define the amino acid sequence of the paratope and the three-dimensional structure of the paratope, and can provide information on the mechanisms of action defining the interaction of an antibody and its antigen.

As used herein, an "epitope" is a part of an antigen that is specifically recognized and bound by an antibody. The amino acids comprising an epitope may be a continuous sequence of amino acid residues within the polypeptide chain of the antigen protein or may be discontinuous amino acid residues that confer conformational specificity upon the three-dimensional structure of the folded antigen.

As used herein, "epitope mapping" is a process of experimentally identifying and characterizing the composition of an epitope within an antigen protein. Epitope mapping is used to define the amino acid sequence of the epitope and the three-dimensional structure of the epitope, and can provide information on the mechanisms of action defining the interaction of an antigen and its antibody.

The present disclosure provides several advantages. First, by reducing a mutational scanning library to include a subset of the most informative amino acid substitutions for a PPI, a new and much smaller mutational scanning library can be prepared, which allows for assessment of new binders with at least a five-fold, six-fold, seven-fold, eight-fold, nine-fold, or even a ten-fold higher throughput, or more, given the same number of direct measurements. For example, by reducing the size of the mutational scanning library necessary to distinguish binding profiles by approximately ten-fold, the number of binders that can be scanned in parallel is increased by ten-fold while holding reagent, labor, and computational costs otherwise constant.

Second, reducing mutational scanning library size can reduce noise in the resulting dataset to improve PPI classification accuracy. In addition, the methods disclosed herein can benefit from a cumulative collection of mutational scanning library data for many PPIs, allowing for training a model to predict a broadly applicable rule set to inform future PPI screens, for example, epitope mapping campaigns. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2C is a schematic diagram of the recombination between SAP expression cassettes mediated by exogenous Cre recombinase indicating PCR amplification of the unique barcode-barcode pair that is a result of the diploid formation event and subsequent recombination of the SAP expression cassettes.

FIG. 6 is a flowchart of a method providing a context-dependent solution for reducing the number of interactions measured when characterizing the binding profiles of a set of protein binders.

FIG. 14 is a section of script of instructions for loading required packages for implementing the methods disclosed herein in a computer system.

FIG. 15 is a section of script of instructions for selecting user-defined settings for implementing the methods disclosed herein in a computer system.

FIG. 16A is a section of script of instructions for calculating affinities per mutation type in a computer system.

FIG. 16B is a section of script of instructions for calculating affinities per mutation site in a computer system.

FIG. 17 is a section of script of instructions for normalizing a colormap in a computer system.

FIG. 18A is a section of script of instructions for hierarchically clustering binding polypeptides based on adjusted affinities in a computer system.

FIG. 18B is a section of script of instructions for hierarchically clustering binding polypeptides based on adjusted affinities in a computer system.

FIG. 19 is a section of script of instructions for forming flat clusters from hierarchical clustering defined by a given linkage matrix in a computer system.

FIG. 20A is a section of script of instructions for defining features, targets, and values to feed into a forward feature group selection (FFGS) classification model in a computer system.

FIG. 20B is a section of script of instructions for defining features, targets, and values to feed into a forward feature group selection (FFGS) classification model in a computer system.

FIG. 21A is a section of script of instructions for designating feature names in a computer system.

FIG. 21B is a section of script of instructions for designating PPI affinity values in a computer system.

FIG. 21C is a section of script of instructions for designating classification targets in a computer system.

FIG. 21D is a section of script of instructions for designating an array of feature groups in a computer system.

FIG. 22A is a section of script of instructions for splitting data into train and test sets in a computer system.

FIG. 22B is a section of script of instructions for splitting data into train and test sets with different random states in a computer system.

FIG. 23 is a section of script of instructions for defining a function to perform forward feature group selection (FFGS) with K-nearest-neighbor (KNN) classification in a computer system.

FIG. 24A is a section of script of instructions for running iterations of FFGS and KNN classification in a computer system.

FIG. 24B is a section of script of instructions for aggregating feature groups selected over iterations of FFGS and KNN classification in a computer system.

FIG. 24C is a section of script of instructions for plotting the frequency of choosing feature groups over a designated number of iterations of FFGS and KNN classification in a computer system.

FIG. 25A is a section of script of instructions for calculating the average number of feature groups selected over a designated number of iterations of FFGS and KNN classification in a computer system.

FIG. 25B is a section of script of instructions for calculating the average training accuracy of a designated number of iterations of FFGS and KNN classification in a computer system.

FIG. 26A is a section of script of instructions for calculating the average test accuracy over a designated number of iterations of FFGS and KNN classification in a computer system.

FIG. 26B is a section of script of instructions for defining a reduced set of feature groups according to the methods disclosed herein in a computer system.

FIG. 26C is a section of script of instructions for subsetting a site-saturation mutagenesis library to a reduced set of feature groups according to the methods disclosed herein in a computer system.

FIG. 27A is a section of script of instructions for designating feature names in a computer system.

FIG. 27B is a section of script of instructions for adjusting PPI affinity values in a computer system.

FIG. 27C is a section of script of instructions for designating classification targets in a computer system.

FIG. 27D is a section of script of instructions for applying a classification model to a subset of a SSM library in a computer system.

FIG. 27E is a section of script of instructions for performing cross-validation in a computer system.

DETAILED DESCRIPTION

Figure 1:
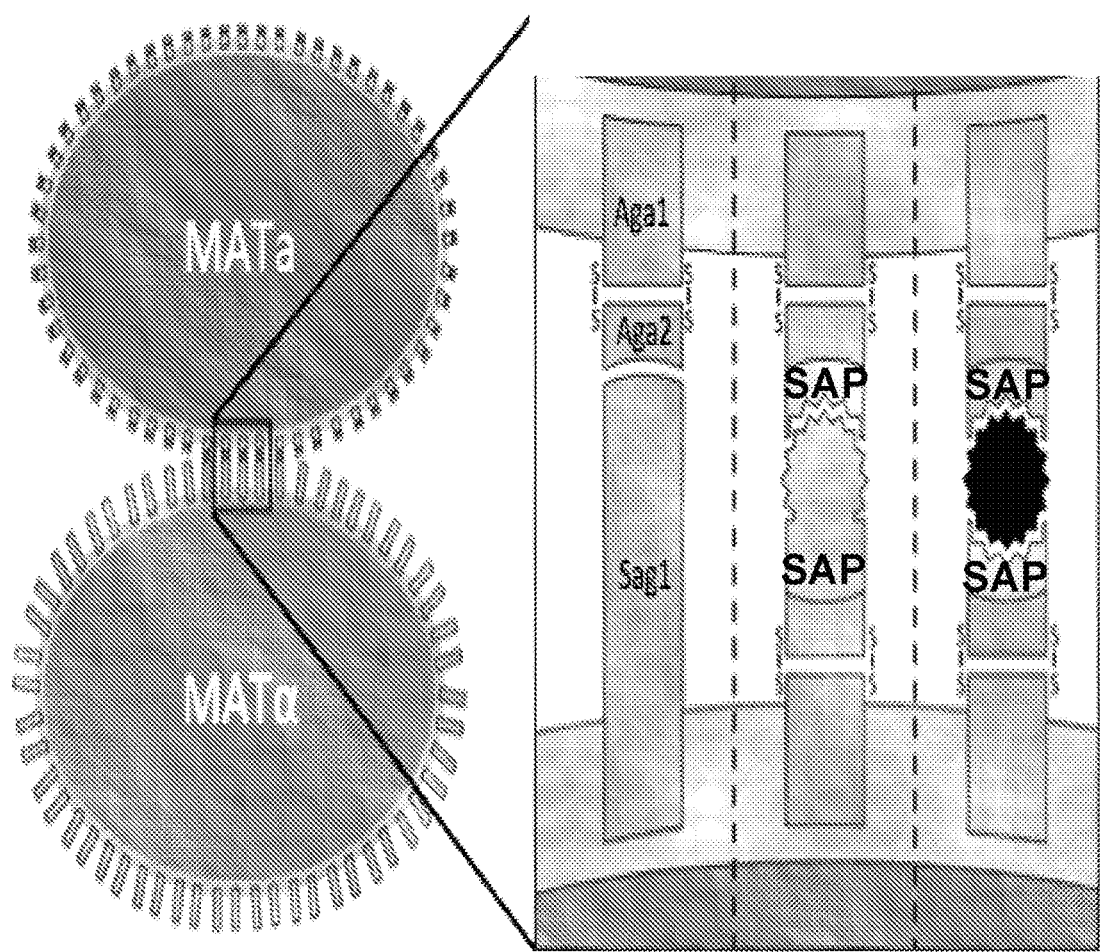
FIG. 1 is a schematic diagram of natural and synthetic yeast agglutination in S. cerevisiae.

The present disclosure provides methods of improving variant polypeptide libraries for screening of protein-protein interactions (PPIs) by excluding variant polypeptides with amino acid substitutions that are predicted to provide little independent information about the binding interface. In particular, the new methods can be used to predict which amino acid substitutions at a given amino acid location in a polypeptide are most and least likely to result in an informative difference in binding when assessing a particular PPI. Thus, the new methods increase the number of informative protein binding partners that can be interrogated by a given screening platform by removing redundant and/or uninformative variant polypeptides from the library. The new methods provide for a ten-fold or more reduction in required library size and a corresponding increase in screening capacity and PPI characterization accuracy. The present disclosure also provides lists of the most informative amino acid substitutions that are predicted by the methods disclosed herein to most significantly affect the interaction of any two protein binding partners.

Measuring Protein-Protein Interactions (PPI)

For a PPI screen of e.g., SSM libraries of protein binding partners, not all amino acid substitutions of the protein binding partners have a highly informative impact on binding, even when a given residue is at the binding interface. Often, multiple substitutions have the same or very similar effect on binding affinity between two protein binding partners. Further, some amino acid substitutions simply have minimal effects on binding affinity. Despite the minimal information content gained from many substitutions, complete or nearly complete saturating mutagenesis is commonly used, because it is not evident a priori which substitutions will provide the most useful information for characterizing a PPI. Therefore, it is often necessary to build large libraries incorporating hundreds or thousands of substitutions at different sites in the proteins, many of which may yield little useful information. This process results in significant cost and time to build such libraries and a large number protein-protein interactions that then need to be screened.

The present disclosure provides methods of predicting which amino acid substitutions at a given residue are most likely to result in an informative difference in binding when assessing a particular PPI. Using this information, screening library sizes can be significantly reduced to exclude amino acid substitutions that are predicted to have a redundant or minimal effect on binding and thus would provide minimal information about the binding interface between two protein binding partners. For a PPI screening platform, cost is essentially linear with the number of measurements performed, as each measurement performed consumes reagents, time, labor, and computational capacity. Accordingly, reducing library size by approximately ten-fold—by including only the most informative amino acid substitutions in a library—will increase throughput by approximately ten-fold for an approximately equivalent cost.

In some embodiments, the methods disclosed herein are performed using a high-throughput synthetic yeast agglutination PPI screening platform. Synthetic yeast agglutination relies on reprogramming yeast sexual agglutination—a naturally-occurring protein-protein interaction—to link protein-protein interaction strength with mating efficiency between a-type recombinant haploid yeast cells and α-type recombinant haploid yeast cells in liquid culture. For a PPI screening platform based on synthetic yeast agglutination, mating efficiency, represented by the number of diploid yeast cells formed in a turbulent liquid culture, is a proxy for PPI affinity. The throughput of the synthetic yeast agglutination PPI screening platform depends on library size. Therefore, reducing library size by excluding amino acid substitutions that are predicted to have a redundant or minimal effect on binding will increase throughput proportionate to the size of the library reduction.

For PPI screening by synthetic yeast agglutination, e.g., as disclosed in U.S. U.S. Pat. Nos. 10,988,759 and 11,136,573, which are incorporated herein by reference in their entireties, each protein of interest (POI) is assigned a unique oligonucleotide molecular barcode, and after diploid formation events, these protein-specific barcodes can be recombined and sequenced to identify the individual synthetic adhesion proteins (SAPs) that mediated the corresponding diploid formation event. Quantifying sequencing reads of unique barcode-barcode combinations acts as a proxy measure of the number of diploid formation events, and thus, PPI affinity.

In some embodiments, PPI affinity is measured by high-throughput methods including synthetic yeast agglutination. FIG. 1 shows a cartoon depiction of natural and synthetic sexual agglutination in a yeast such as S. cerevisiae. At the left, the MATa and MATα haploids are shown at the top and bottom, respectively. The cell wall of each haploid cell is shown in grey. In a turbulent liquid culture, MATa and MATα haploid cells stick to one another due to the binding of sexual agglutinin proteins, which allows them to mate. The native sexual agglutinin proteins consist of Aga1 and Aga2, expressed by MATa cells, and Sag1, expressed by MATα cells. Aga1 and Sag1 form GPI anchors with the cell wall and extend outside of the cell wall with glycosylated stalks (see left frame of inset). Aga2 is secreted by MATa cells and forms a disulfide bond with Aga1. The interaction between Aga2 and Sag1 is essential for wild-type sexual agglutination.

The native sexual agglutinin interaction can be replaced with an engineered one by expressing Aga1 in both mating types and fusing complementary binders to Aga2 (see middle frame of inset). In this case, the SAP comprises the fusion of Aga2 and the binder of interest. Interaction of binders therefore mediates adhesion, and subsequently the agglutination process. Instead of direct agglutination, it may be possible to express binders for a multivalent target, such that agglutination and mating only occurs in the presence of the target (see right frame of inset).

In some embodiments, the SAPs of first and second expression cassettes of first and second nucleic acid constructs, respectively, bind to a cell wall GPI anchored protein. In some embodiments, the SAPs can be fused to a cell wall GPI anchored protein or fused to a protein that forms a disulfide bond with a cell wall GPI anchored protein. In some embodiments, the SAP of a first expression cassette of a first nucleic acid construct is fused to the sexual agglutination protein Aga2, and the SAP of a first expression cassette of a second nucleic acid construct is fused to the sexual agglutination protein Aga2.

Figure 2A:
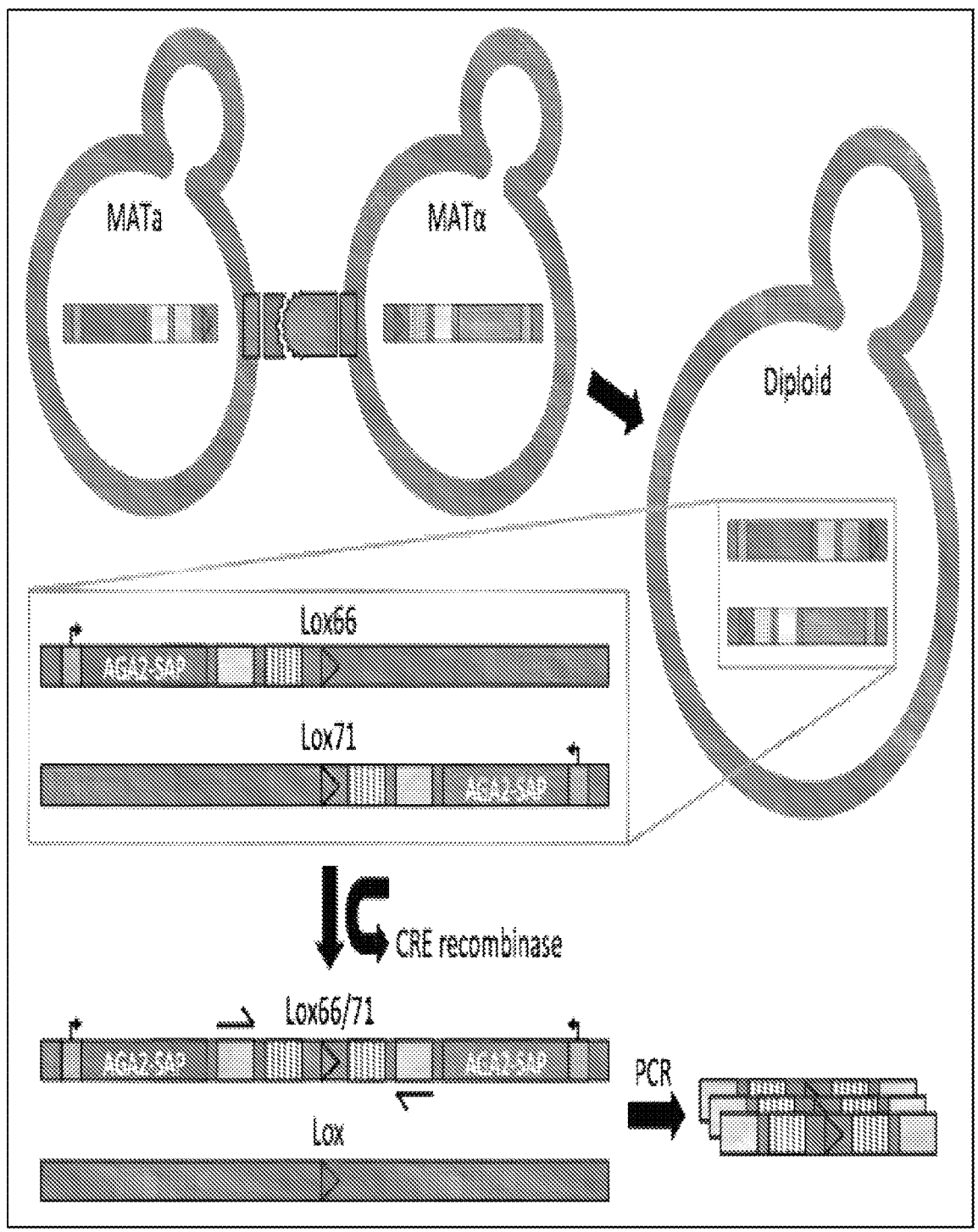
FIG. 2A is a schematic diagram of the recombination between SAP expression cassettes mediated by exogenous Cre recombinase.

FIG. 2A shows a schematic of the Cre recombinase translocation scheme for high throughput analysis of display pair interactions. Here, a mating between a single recombinant MATa yeast strain and a single recombinant MATα yeast strain is shown. For a batched mating assay, however, a library of displayer cells of each mating type would be used (each comprising a library of SAPs fused to Aga2). Each MATa and MATα haploid cell contains a SAP fused to Aga2 integrated into a target chromosome (for example, chromosome III). Upon mating, both copies of the target chromosome are present in the same diploid cell. In addition to the SAP/Aga2 cassette, each copy of the target chromosome has a unique primer binding site, one of a plurality of unique oligonucleotide barcodes operably linked to the particular SAP, and a lox recombination site.

The plurality of oligonucleotide barcodes can be synthesized and assembled with the library of SAP expression cassettes such that a single SAP species is operably linked to a plurality of unique oligonucleotide barcodes. Upon expression of Cre recombinase, a chromosomal translocation occurs at the lox sites, resulting in a juxtaposition of the primer binding sites and barcodes onto the same copy of the target chromosome. A PCR is then performed to amplify a region of the chromosome containing the barcodes from both SAPs, such that sequences comprising unique barcode-barcode pairs, each representing a diploid formation event, are amplified. In a batched mating, the result is a pool of fragments, each containing the unique barcode-barcode pair associated with two SAPs that were responsible for the single diploid formation event. Paired-end next generation sequencing is then used to match the barcodes and determine the number of diploid formation events mediated by that SAP pair.

Figure 2B:
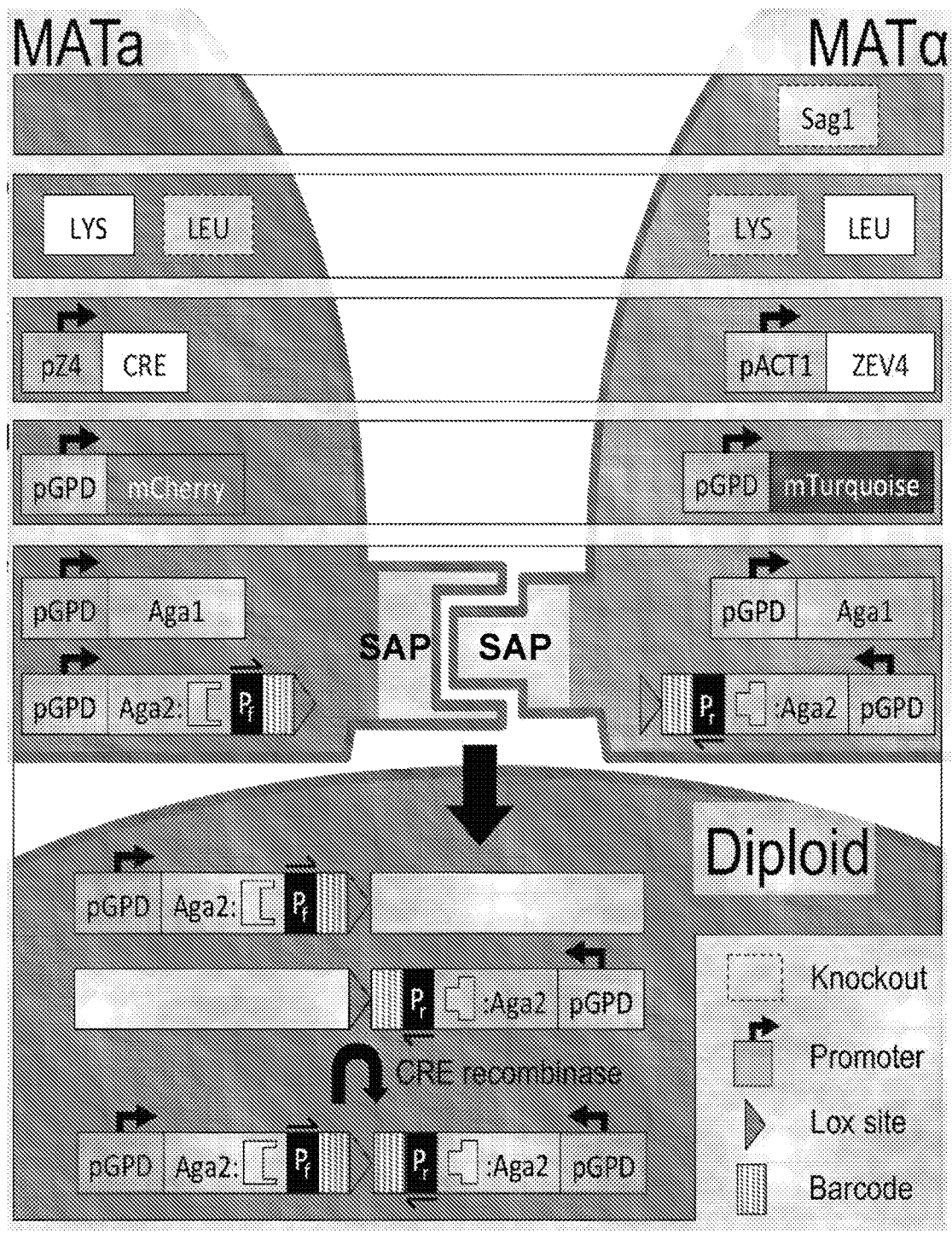
FIG. 2B is a more detailed schematic of the recombination between SAP expression cassettes mediated by exogenous Cre recombinase.

FIG. 2B shows another schematic of the Cre recombinase translocation scheme for high throughput analysis of display pair interactions. The a-agglutinin, Sag 1, is knocked out in MATa cells to eliminate native agglutination. MATa and MATα cells are able to synthesize lysine or leucine, respectively. Diploids can then be selected for in media lacking both amino acids. MATa cells express ZEV4, a βE inducible transcription factor that activates Cre recombinase expression in diploid cells. MATa and MATα cells express mCherry and mTurquoise, respectively, for identification of strain types with flow cytometry. MATa and MATα cells constitutively express Aga1 along with a uniquely barcoded SAP fused to Aga2. When Cre recombinase expression is induced in diploids with βE, a chromosomal translocation at lox sites consolidates both SAP-Aga2 fusion expression cassettes onto the same chromosome. A single fragment containing the unique barcode-barcode sequence associated with that diploid formation event is then amplified by PCR with primers annealing to Pf and Pr (primers specific to the primers from the first and second nucleic acid constructs integrated at the genomic target site) and sequenced to quantify the number of diploid formation events and identify the interacting SAP pair.

FIG. 2C shows a schematic of the CRE recombinase translocation scheme for high throughput analysis for interactions between synthetic adhesion proteins from a library to library screen. When CRE recombinase expression is induced in diploids with βE, a chromosomal translocation at lox sites consolidates both SAP-Aga2 expression cassettes onto the same chromosome. A single fragment containing the unique barcode-barcode sequence associated with that diploid formation event is then amplified by PCR with primers annealing to primer binding sites from each of the first and second nucleic acid constructs and sequenced (for example, using a paired end analysis of next generation sequencing) to quantify the number of diploid formation events and identify the interacting SAP pair.

In some embodiments, the method comprises a target library comprising a plurality of target polypeptide variants and a binder library comprising a plurality of binder polypeptide variants. The target polypeptide variants and the binder polypeptide variants can be user-designated or randomly added mutants of a protein and the wild-type protein. In some embodiments, the amino acid substitutions may be generated by site saturation mutagenesis (SSM) to produce an SSM library of the target polypeptide and the binder polypeptide. In some embodiments, the target polypeptide variants and the binder polypeptide variants can be generated by alanine scanning. In some embodiments, the target polypeptide variants and the binder polypeptide variants can be generated by random mutagenesis, such as with error prone PCR, or another method to introduce variation into the amino acid sequence of the expressed protein. The target library comprising a plurality of target polypeptide variants and the binder library comprising a plurality of binder polypeptide variants are assayed for binding affinity, such that affinity is measured for interaction between each of the plurality of target polypeptide variants and each of the plurality of binder polypeptide variants individually, in a parallelized high-throughput manner.

In some embodiments, the target polypeptide variants and the binder polypeptide variants are full-length proteins. In some embodiments, the target polypeptide variants and the binder polypeptide variants are truncated proteins. In some embodiments, the target polypeptide variants and the binder polypeptide variants are fusion proteins. In some embodiments, the target polypeptide variants and the binder polypeptide variants are tagged proteins. Tagged proteins include proteins that are epitope tagged, e.g., FLAG-tagged, HA-tagged, His-tagged, Myc-tagged, among others known in the art. The target polypeptide variants and the binder polypeptide variants can each be any of the following: a full-length protein, truncated protein, fusion protein, tagged protein, or combinations thereof.

In some embodiments, the binder polypeptide variants are antibodies or truncated portions of antibody polypeptides. In some embodiments, the library of binder polypeptide variants is a library of antibodies, truncated antibody polypeptides, or a library of antibody mutants generated by site saturation mutagenesis, alanine scanning, or other methods well known in the art. Antibodies, also known as immunoglobulins, are relatively large multi-unit protein structures that specifically recognize and bind to a unique molecule or molecules. For most antibodies, two heavy chain polypeptides of approximately 50 kDA and two light chain polypeptides of approximately 25 kDA are linked by disulfide bonds to form the larger Y-shaped multi-unit structure. Variable and hypervariable regions representing amino-acid sequence variability at the tips of the Y-shaped structure confer specificity for a given antibody to recognize its target.

In some embodiments, the binder polypeptide variants are variants of a single-chain variable fragment (scFv), a fusion protein of the variable regions of the heavy (VH) and light chains (VL) of an immunoglobulin connected by short linker peptides. In some embodiments, the library of binder polypeptide variants is a library of scFvs or a library of scFvs mutants generated by site saturation mutagenesis, alanine scanning, or other methods well known in the art.

In some embodiments, the binder polypeptide variants are variants of an antigen-binding fragment (Fab), a region of an antibody that binds to an antigen. A Fab may comprise one constant and one variable domain of each of the heavy and the light chain, and includes the paratope region of the antibody. In some embodiments, the library of binder polypeptide variants is a library of Fabs or a library of Fab mutants generated by site saturation mutagenesis, alanine scanning, or other methods well known in the art.

In some embodiments, the binder polypeptide variants are variants of a portion of a single domain antibody, or VHH, the antigen-binding fragment of a heavy chain only antibody. A VHH comprises one variable domain of a heavy-chain antibody. In some embodiments, the library of binder polypeptide variants is a library of VHHs or a library of VHH mutants generated by site saturation mutagenesis, alanine scanning, or other methods well known in the art.

In some embodiments, the binder polypeptide variants are variants of an E3 ubiquitin ligase. E3 ubiquitin ligases include MDM2, CRL4$^{CRBN}$, SCF$^{\beta TrCP}$, UBE3A, and many other species that are well known in the art. E3 ubiquitin ligases recruit the E2 ubiquitin-conjugating enzyme that has been loaded with ubiquitin, recognize its target protein substrate, and catalyze the transfer of ubiquitin molecules from the E2 to the protein substrate for subsequent degradation by the proteasome complex. In some embodiments, the library of binder polypeptide variants is a library of E3 ubiquitin ligases or a library of E3 ubiquitin ligase mutants generated by site saturation mutagenesis, alanine scanning, or other methods well known in the art.

In some embodiments, the target polypeptide variants are variants of an antigen. An antigen is a molecule or molecular structure that is targeted by an antibody. Antigens are typically proteins, polypeptides, or polysaccharides that are targeted by a specific corresponding antibody. An antigen comprises an epitope, the portion of the antigen that is recognized by, and confers specificity to, the antigen's corresponding antibody. In some embodiments, the library of target polypeptide variants is a library of antigens or a library of antigen mutants generated by site saturation mutagenesis, alanine scanning, or other methods well known in the art.

In some implementations, the second binding partner is a target protein comprising a degron. In other implementations, the library of second binding partners is a library of proteins comprising degrons or a library of proteins comprising degron mutants generated by site saturation mutagenesis, among other methods. A degron is a portion of a protein that mediates regulated protein degradation, in some cases by the ubiquitin proteasome system. Degrons may include short amino acid motifs; post-translational modifications, e.g., phosphorylation; structural motifs; sugar modifications; among others.

Reducing Mutation Space for Library-by-Library Screening of PPI

In some embodiments, the mutation space for a PPI screening method is reduced by performing a library-by-library PPI screening of an SSM library of target polypeptide variants against an SSM library of binder polypeptide variants as described herein, e.g., by synthetic yeast agglutination. Binding affinities are measured, e.g., as $-\log_{10}(K_d)$ in nM for each target/binder combination, where $K_d$ is the dissociation constant between the protein binding partners. Binders are clustered into groups using a correlation distance metric and, for example, agglomerative hierarchical clustering. In some embodiments, binders that do not cluster into groups are removed from the further analysis.

Feature selection can be used to reduce the size of the library of polypeptide variants. Feature selection is a process of selecting a subset of relevant features (variables, predictors) for use in model construction. Feature selection techniques can be used to simplify models to facilitate interpretation by users, to shorten training times in machine learning models, to reduce dimensionality in a model, i.e., to reduce the number of pair-wise interactions in a model, or to improve the compatibility of data with a learning model class.

A premise of feature selection is that the data contain some features that are either redundant or irrelevant, and can thus be removed without incurring a significant loss of information. In the context of the present disclosure, the redundancy is among amino acid substitutions of a polypeptide binding partner that have little to no impact on binding of the polypeptide to its corresponding binding partner. Feature selection methods that can be used for the methods disclosed herein include, for example, exhaustive, best first, simulated annealing, greedy forward selection, greedy backward elimination, particle swarm optimization, targeted projection pursuit, scatter search, variable neighborhood search, minimum-redundancy-maximum-relevance (mRMR), joint mutual information (JMI), correlation feature selection (CFS), among others. In some embodiments, forward feature group selection (FFGS) is used.

Feature groups can be designated a priori, with each polypeptide variant of the library of polypeptide variants that shares the same original-to-mutated amino acid substitution across all sites in the polypeptide being designated as a feature group. For example, for an SSM library of a target polypeptide, all alanine to lysine mutations across all sites in the antigen SSM library can be designated as a single feature group labeled by its 1-letter abbreviations "AK," representing alanine to lysine substitutions.

In some embodiments, starting with no features, the feature group that results in the greatest gain in performance can be added to the model in each round of selection until no further gain is achieved. In some embodiments protein binding partners of a library are classified in each round of selection using a K-Nearest Neighbors (KNN) classifier. In some embodiments, model performance is measured via classification accuracy, i.e., the proportion of times the model is able to correctly classify binding partners of a library into groups that match the hierarchical clustering performed on the full protein binder mutant library.

In some embodiments, the model is run with feature selection for 10, 20, 30, 40, 50, 60, 70, 80, 90, 100, 200, 300, 400, 500, 1000, or more iterations. For example, the model can be run using FFGS for 100 iterations. In some embodiments, each time the model is run the dataset is split into a different stratified train-test split to produce different results. For example, a top set of feature groups that were selected in 25% of the 100 iterations can comprise a core subset of features in the reduced SSM library. In some embodiments, to ensure coverage across all mutation types, the most frequently selected feature group for each wild-type amino acid that was not already selected as part of the core subset is added to the final reduced feature set. The accuracy of the trained model can be calculated for each of the iterations, for example, 100 iterations, using the test set reserved from the train-test split. In some embodiments, using the results of the 100 or more iterations of the model and train-set split, the reduced set of feature groups can be used to reduce the dimensionality of additional libraries of other protein binding partners.

Context-Dependent Solution

In some embodiments, the methods disclosed herein are used to reduce the dimensionality of a PPI screen of two particular protein binding partners. For example, the methods disclosed herein can be used to reduce the number of antibody variants screened against a library of binder variants. In some embodiments, a first library of protein binding partner variants is built including many residues and substitutions, for example, an SSM library. Binding of members of this SSM library can then be measured against a small set of binding partners. Based on the resulting dataset, a second library of protein binding partners can be built for the same protein only including a subset of substitutions that resulted in differential binding in the first assay, and after which binding against a larger number of binders can be measured according to the methods disclosed herein. This method yields a reduced set of interactions that need to be screened for a particular protein to determine the residues involved at the interface of those interactions.

Figure 3:
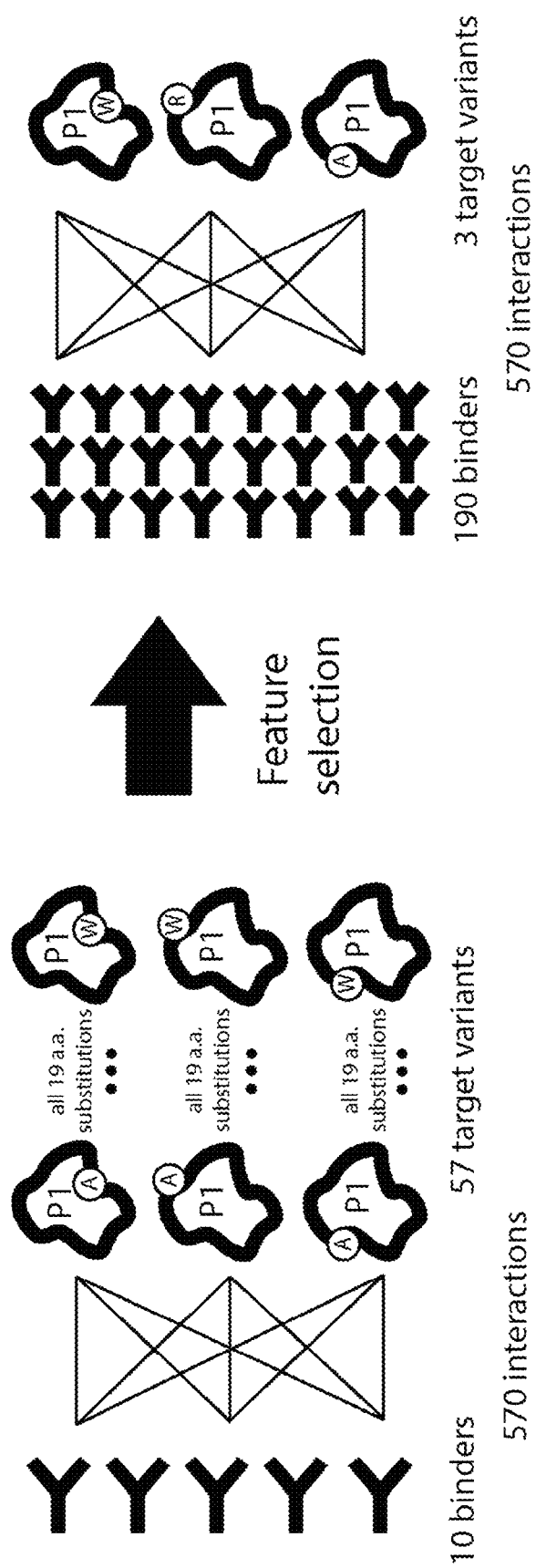
FIG. 3 is a schematic representation of a context-dependent solution for reducing the number of interactions measured when characterizing the binding profiles of a set of 200 protein binders.

These methods are illustrated in FIG. 3, which shows a set of 10 binders screened against all 19 amino acid substitutions at three surface-exposed residue sites in a target protein binding partner. This screening involves the measurement of 570 interactions (10*19*3=570) between binding protein binding partners and target protein binding partner variants. The resulting data can be analyzed according to the methods disclosed herein to determine which amino acid substitutions had the highest information content to distinguish binding profiles for all 10 binders. This analysis determines that a smaller set of three target protein binding partner variants with unique substitutions at each residue site can distinguish binding profiles for all 10 binders. The smaller set of three target variants can then be screened against an additional 190 binders to distinguish their binding profile requiring the measurement of 570 additional interactions. In this example, a total of 1,140 interactions were required to characterize the binding profiles of 200 binders.

Absent the methods disclosed herein, e.g., feature selection and dimensionality reduction, a total of 11,400 interaction would have been required to screen all 200 binders against all amino acid substitutions at the three residue sites.

The context-dependent solution used to reduce the dimensionality of a PPI screen of two particular protein binding partners is further illustrated in the flowchart of FIG. 6. A target library comprising a plurality of target polypeptide variants of a target protein is provided. The target library can include variants of a particular protein, e.g., variants of an antibody. Binding affinities between each target polypeptide variant of the target library and each of a plurality of binding polypeptides are measured. In some embodiments, the binding affinities are measured by synthetic yeast agglutination, e.g., AlphaSeq™. Based on the binding affinities, the binding polypeptides are clustered using a correlation distance metric and agglomerative hierarchical clustering to identify one or more groups of related binding profiles. Feature selection is applied to the target library to identify a subset of target polypeptide variants that distinguish binding profiles for binding to the target protein. Finally, a list of amino acid substitutions that affect protein-protein interactions is provided, which is a subset of the target polypeptide variants that most affect binding affinities relative to the wild-type target polypeptide.

General Solution

According to the methods disclosed herein, multiple datasets can be collected for a plurality of different proteins involving a large number of mutational libraries screened against their respective binders. In some embodiments, results including datasets for a plurality of different proteins can be generalized to predict a universal set of amino acid substitutions that are more likely to result in a reduction or loss of binding between any two protein binding partners. Based on these aggregate data, amino acid substitutions that are more likely to result in a reduction or loss of binding for any protein-protein interaction between protein binding partners can be predicted.

Figure 4:
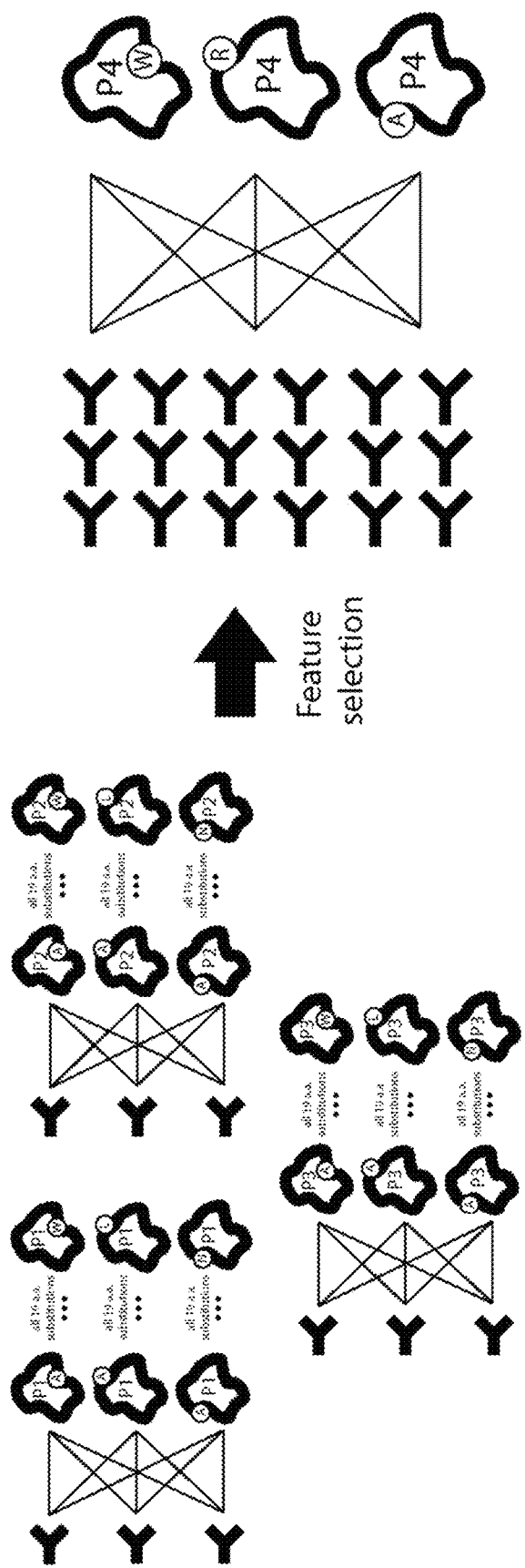
FIG. 4 is a schematic representation of a general solution for reducing the number of interactions measured when characterizing the binding profiles of a set of protein binders.

As shown in FIG. 4, binding data can be generated between protein binders and variant libraries corresponding to different target proteins ("P1," "P2," and "P3" in FIG. 4). The resulting data can be analyzed according to the methods disclosed herein, e.g., by feature selection and dimensionality reduction, to determine which amino acid substitutions had the highest information content to distinguish binding profiles across all target proteins. Based on the analysis according to the methods disclosed herein, a reduced set of substitutions for each amino acid can then be applied to a new target protein ("P4" in FIG. 4), enabling the characterization of a larger number of protein binders as a general method of reducing dimensionality for libraries of protein binding partner variants.

Figure 7:
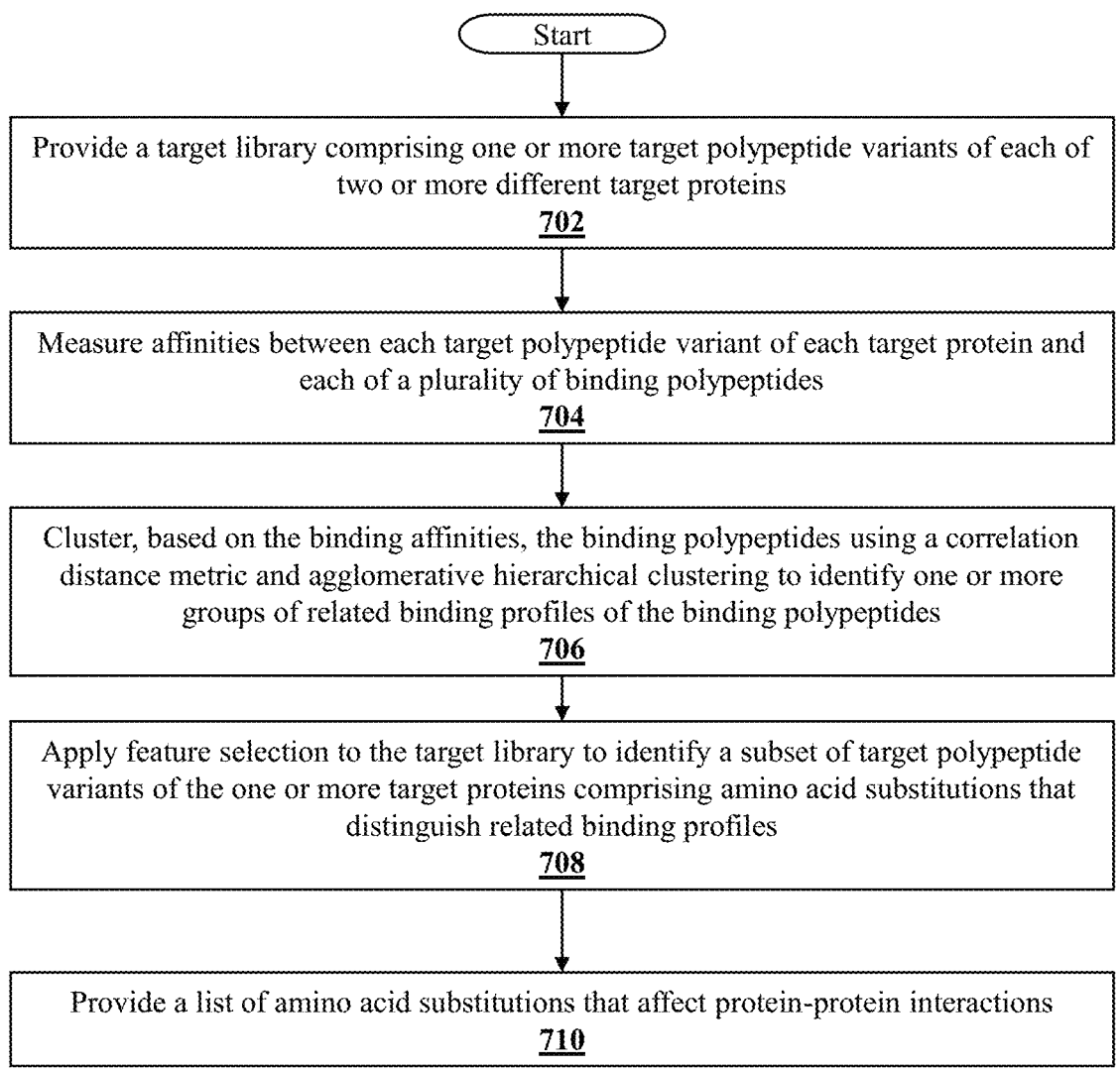
FIG. 7 is a flowchart of a method providing a general solution for reducing the number of interactions measured when characterizing the binding profiles of a set of protein binders.

The general solution used to predict a set of amino acid substitutions that are more likely to result in a reduction or loss of binding for any two protein binding partners is further illustrated in the flowchart of FIG. 7. A target library comprising one or more target polypeptide variants of each of two or more different target proteins is provided. Affinities between each target polypeptide variant of each target protein and each of a plurality of binding polypeptides are measured. In some embodiments, the binding affinities are measured by synthetic yeast agglutination, e.g., AlphaSeq™. Based on the binding affinities, the binding polypeptides are clustered using a correlation distance metric and agglomerative hierarchical clustering to identify one or more groups of related binding profiles of the binding polypeptides. Feature selection is applied to the target library to identify a subset of target polypeptide variants of the one or more target proteins comprising amino acid substitutions that distinguish related binding profiles. Finally, a list of amino acid substitutions that affect protein-protein interactions is provided, which is a subset of the variants that most affect binding affinities relative to each of the wild-type target polypeptides. The amino acid substitutions identified by the general solution are predicted to be the most informative for impacting binding affinity between any two generalized protein binding partners.

Table 1, below, lists feature groups identified by the methods disclosed herein as being most informative for impacting binding affinity between any two generalized protein binding partners.

TABLE 1

Selected Feature Groups

| Original amino acid residue | Mutated amino acid residue |
|---|---|
| A | T |
| A | I |
| A | S |
| A | L |
| A | D |
| D | V |
| E | K |
| F | I |
| F | P |
| G | N |
| G | Y |
| G | L |
| H | P |
| I | E |
| K | E |
| L | H |
| M | W |
| N | L |
| P | Q |
| Q | G |
| R | K |
| S | H |
| T | R |
| V | G |
| W | N |
| Y | A |

As disclosed herein, feature groups can be described as the combination of the parental target protein amino acid residue and the mutant amino acid residue. For example, the "GN" feature group refers to the set of polypeptide variants of the parental target protein wherein each glycine amino acid residue position of the parental target protein sequence has been mutated to an asparagine. As determined by the methods disclosed herein, the most informative feature groups for distinguishing groups of related binding profiles for binding to a target protein, in descending order of significance, include GN, GY, AT, AI, AS, FI, GL, LH, FP, AL, and AD. Additionally, in order to saturate the polypeptide variants of the parental target protein and ensure that each position of the parental target protein is interrogated, the most informative feature groups for the remaining amino acid residues (excluding cysteine) include DV, EK, HP, IE, KE, MW, NL, PQ, QG, RK, SH, TR, VG, WN, and YA.

In some embodiments, a set of the most informative feature groups comprises AT, DV, EK, FP, GN, HP, IE, KE, LH, MW, NL, PQ, QG, RK, SH, TR, VG, WN, and YA. In some embodiments, a set of the most informative feature groups comprises AT, DV, EK, FP, GN. In some embodiments, the set of the most informative feature groups further comprises HP, IE, KE, LH, MW. In some embodiments, the set of the most informative feature groups further comprises NL, PQ, QG, RK, SH. In some embodiments, the set of the most informative feature groups further comprises TR, VG, WN, YA, and GY. In some embodiments, the set of the most informative feature groups further comprises AI, AS, GL, FP, AL, and AD.

Computing Environment and Algorithms

The methods disclosed herein can be embodied in any suitable programming language and executed on any suitable computing system. In some implementations, the methods disclosed here herein are written used the Python programming language. In some implementations, the methods disclosed herein are executed on a cloud computing platform, for example, a virtual machine. In an implementation, the methods disclosed herein are executed on a virtual machine provisioned by AWS EC2 (m5.12×large). The Python packages numpy and pandas can be used for general data manipulation; hierarchical clustering was performed using the implementation in the scipy.cluster package. The sklearn package can be utilized for KNN-classification and cross-validation algorithms. Forward feature group selection can be performed as implemented in the cobox Python package. Representative scripts for executing the methods disclosed herein are provided in FIGS. 14-27E.

Figure 5:
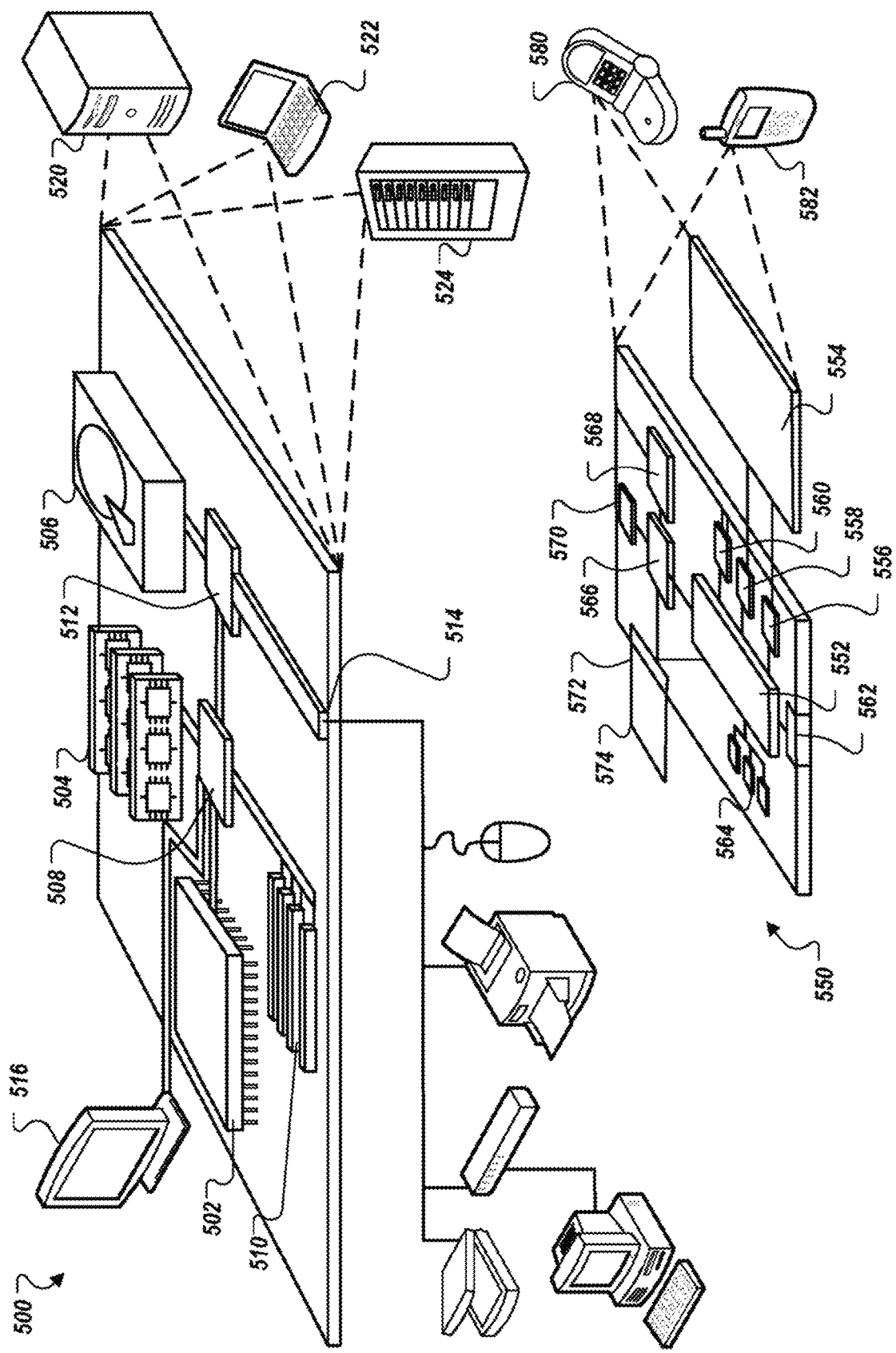
FIG. 5 is a diagram of general computer system components that can be used to implement the methods for reducing the size of the respective libraries for a library-by-library screen of protein-protein interactions (PPIs) as described herein.

FIG. 5 is a diagram of a computer system 500 that can be used to implement a method for reducing the size of the respective libraries for a library-by-library screen of protein-protein interactions (PPIs).

Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, and other similar computing devices. Additionally, computing device 500 or 550 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and can be mounted on a common motherboard or in other manners as appropriate. The processor 502 can process instructions for execution within the computing device 500, including instructions stored in the memory 504 or on the storage device 506 to display graphical information for a graphical user interface (GUI) on an external input/output device, such as display 516 coupled to high speed interface 508. In other implementations, multiple processors and/or multiple buses can be used, as appropriate, along with multiple memories and types of memory. Also, multiple computing devices 500 can be connected, with each device providing portions of the necessary operations, e.g., as a server bank, a group of blade servers, or a multi-processor system.

The memory 504 stores information within the computing device 500. In one implementation, the memory 504 is a volatile memory unit or units. In another implementation, the memory 504 is a non-volatile memory unit or units. The memory 504 can also be another form of computer-readable medium, such as a magnetic or optical disk.

The storage device 506 provides mass storage for the computing device 500. In one implementation, the storage device 506 can be or contain a tangible, computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low speed controller 512 manages lower bandwidth intensive operations. Such allocation of functions is only an example. In one implementation, the high-speed controller 508 is coupled to memory 504, display 516, e.g., through a graphics processor or accelerator, and to high-speed expansion ports 510, which can accept various expansion cards (not shown). In another implementation, low-speed controller 512 is coupled to storage device 506 and low-speed expansion port 514. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

Computing device 550 includes a processor 552, memory 564, and an input/output device such as a display 554, a communication interface 566, and a transceiver 568, among other components. The device 550 can also be provided with a storage device, such as a micro-drive or other device, to provide additional storage. Each of the components 550, 552, 564, 554, 566, and 568, are interconnected using various buses, and several of the components can be mounted on a common motherboard or in other manners as appropriate.

The processor 552 can execute instructions within the computing device 550, including instructions stored in the memory 564. The processor can be implemented as a chipset of chips that include separate and multiple analog and digital processors. Additionally, the processor can be implemented using any of a number of architectures. For example, the processor 510 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 550, such as control of user interfaces, applications run by device 550, and wireless communication by device 550.

Processor 552 can communicate with a user through control interface 558 and display interface 556 coupled to a display 554. The display 554 can be, for example, a TFT (Thin-Film-Transistor Liquid Crystal Display) display or an OLED (Organic Light Emitting Diode) display, or other appropriate display technology. The display interface 556 can comprise appropriate circuitry for driving the display 554 to present graphical and other information to a user. The control interface 558 can receive commands from a user and convert them for submission to the processor 552. In addition, an external interface 562 can be provided in communication with processor 552, so as to enable near area communication of device 550 with other devices. External interface 562 can provide, for example, for wired communication in some implementations, or for wireless communication in other implementations, and multiple interfaces can also be used.

The memory 564 stores information within the computing device 550. The memory 564 can be implemented as one or more of a computer-readable medium or media, a volatile memory unit or units, or a non-volatile memory unit or units. Expansion memory 574 can also be provided and connected to device 550 through expansion interface 572, which can include, for example, a SIMM (Single In Line Memory Module) card interface. Such expansion memory 574 can provide extra storage space for device 550, or can also store applications or other information for device 550. Specifically, expansion memory 574 can include instructions to carry out or supplement the processes described above, and can also include secure information. Thus, for example, expansion memory 574 can be provided as a security module for device 550, and can be programmed with instructions that permit secure use of device 550. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552 that can be received, for example, over transceiver 568 or external interface 562.

Device 550 can communicate wirelessly through communication interface 566, which can include digital signal processing circuitry where necessary. Communication interface 566 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 568. In addition, short-range communication can occur, such as using a Bluetooth, Wi-Fi, or other such transceiver (not shown). In addition, GPS (Global Positioning System) receiver module 570 can provide additional navigation- and location-related wireless data to device 550, which can be used as appropriate by applications running on device 550.

Device 550 can also communicate audibly using audio codec 560, which can receive spoken information from a user and convert it to usable digital information. Audio codec 560 can likewise generate audible sound for a user, such as through a speaker, e.g., in a handset of device 550. Such sound can include sound from voice telephone calls, can include recorded sound, e.g., voice messages, music files, etc. and can also include sound generated by applications operating on device 550.

Various implementations of the systems and methods described here can be realized in digital electronic circuitry, integrated circuitry, special purpose logic circuitry, e.g., an FPGA (field programmable gate array) or an ASIC (application specific integrated circuit), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

As used herein, the terms "machine-readable medium" "computer-readable medium" refers to any computer program product, apparatus and/or tangible device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

EXAMPLES

The invention is further described in the following examples, which do not limit the scope of the invention described in the claims.

Example 1: Reducing a Library of TIGIT Variants

A target SSM library was created by mutating sites in the wild-type sequence of the TIGIT antigen to one of 19 alternative amino acids. TIGIT, which is also called the T cell immunoreceptor with Ig and ITIM domains, is an immune receptor present on some T cells and natural killer cells (NK). It is also identified as WUCAM and Vstm3. TIGIT binds to CD155 (PVR) on dendritic cells (DCs), macrophages, etc. with high affinity, and also to CD112 (PVRL2) with lower affinity.

Mutations to cysteine were excluded to avoid the formation of disulfide bridges that could disrupt the target structure. Yeast display libraries developed using synthetic yeast agglutination, as discussed above, were then used to measure predicted binding affinities as $-\log_{10}(K_d)$ in nM between each antibody/antigen combination, where $K_d$ is the dissociation constant. The lower the value of $K_d$, the higher the affinity between the antibody and the antigen. Antibodies with a wild-type predicted affinity less than 3, i.e., those that reasonably bound to the original target, were retained for subsequent analyses. All non-wild-type mutations in the SSM library without predicted affinities were imputed with values 2-logs weaker than the wild-type binding affinity.

Adjusted affinities were calculated by subtracting the wild-type affinities from the predicted affinities. The absolute value of the adjusted affinities were averaged per site in the SSM library for each antibody. To standardize the affinities, each affinity value was divided by both the mean adjusted affinity per binder and the mean adjusted affinity per site in the SSM. At this stage, only antibodies with measurable baseline binding to the target and for which binding was ablated by target mutations at one or more sites (i.e., antibodies for which determining epitope residues could be reasonably inferred) remain in the dataset for analysis. In particular, only antibodies that had at least one site with ablated binding with a mean adjusted affinity greater than 1.9 were retained. Binders were clustered into groups using a correlation distance metric and agglomerative hierarchical clustering. Binders that did not cluster into groups were removed from the final set.

Binders were then separately classified into groups using a reduced SSM library in an attempt to recapture the hierarchical clusters generated above with the full SSM dataset. Sites were split into their individual mutation combinations, and codons that coded for the same amino acid change were averaged. Mutations that resulted in adjusted affinities greater than 2 across more than 90% of the antibody candidates were discarded as uninformative.

To reduce the size of the antigen SSM library, forward feature group selection (FFGS) was performed using the Python package eo-box (github.com/benmack/eo-box), an extension of mlxtend, to add groups of mutations to the classification model under a greedy forward selection strategy. Feature groups were designated a priori, grouping together mutations with the same wild-type amino acid and mutated amino acid combination. For example, all alanine to lysine mutations across all sites in the antigen SSM library constituted one group labeled by their 1-letter abbreviations AK. Starting with no features, the feature group that resulted in the greatest gain in performance was added to the model in each round of selection until no further gain was achieved. Binders were classified in each round using a K-Nearest Neighbors (KNN) classifier with k=5 neighbors and 5-fold stratified cross-validation from the Python module sklearn.

Model performance was measured via classification accuracy, or the proportion of times the model was able to correctly classify antibodies into groups that matched the hierarchical clustering performed on the full antigen SSM library. The model was run with FFGS for 100 iterations, each time splitting the dataset into a different stratified train-test split to produce different results. A top set of feature groups that were selected in 25% of the 100 iterations made up the core subset of features in the reduced SSM library. To ensure coverage across all mutation types, the most frequently selected feature group for each wild-type amino acid that was not already selected as part of the core subset was added to the final reduced feature set. The accuracy of the trained model was calculated for each of the 100 iterations using the test set reserved from the train-test split. Finally, the reduced set of feature groups was used to subset the SSM libraries of other antigen targets and classify different sets of antibodies.

Figure 8:
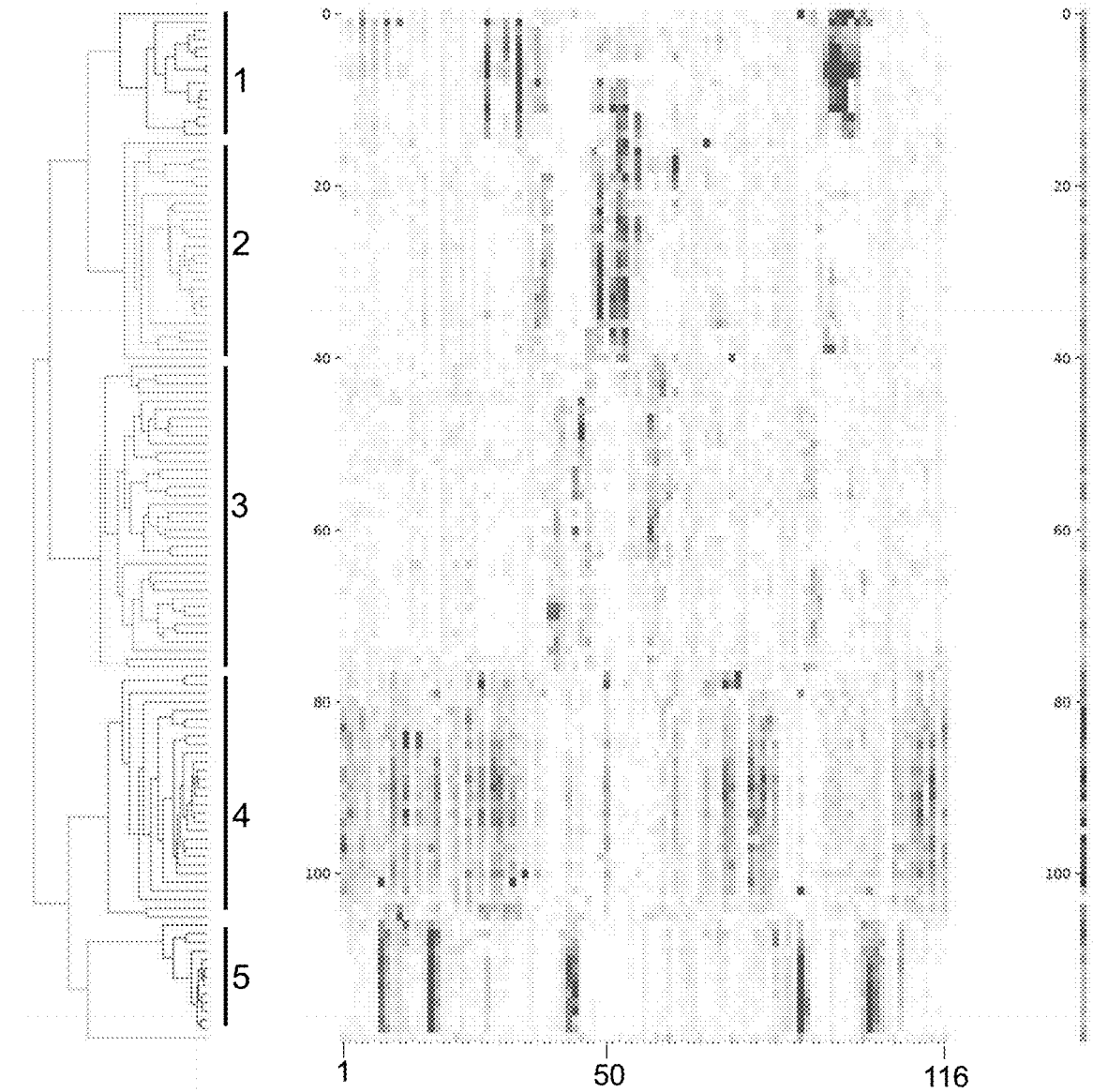
FIG. 8 is a heatmap of results from an epitope mapping experiment using hierarchical clustering results for the antigen target TIGIT (T cell immunoreceptor with Ig and ITIM domains) using a full site-saturation mutagenesis (SSM) library. Each column of the heatmap is a mutated site in the SSM and each row is an antibody candidate. Darker regions of the heatmap indicate higher adjusted binding affinity values (higher $K_d$). These regions indicate putative epitopes. Adjusted binding affinities of each antibody to the wild-type antigen sequence are shown in the single column along the right. Again, darker values indicate higher adjusted binding affinity values. Each cluster of the dendrogram, at left, represents a different epitope profile clustered via a correlation distance metric and agglomerative hierarchical clustering.
Figure 9:
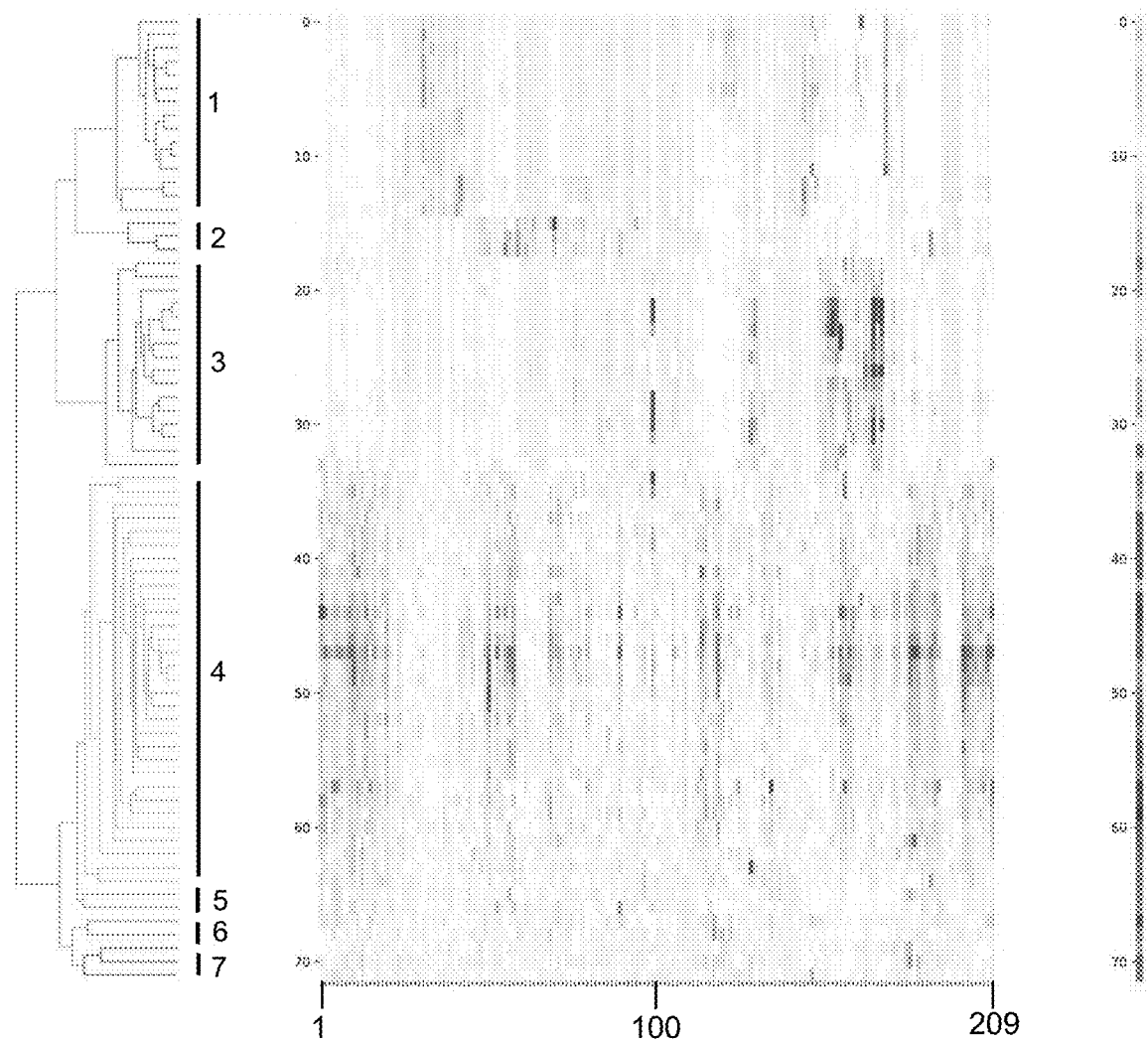
FIG. 9 is a heatmap of results from an epitope mapping experiment using hierarchical clustering results for the SARS-CoV2 receptor-binding domain (RBD). Each column of the heatmap is a mutated site in the protein and each row is a binding site candidate. Darker regions of the heatmap indicate higher adjusted binding affinity values (higher $K_d$). These regions indicate putative binding sites. Adjusted binding affinities of each binder to the wild-type RBD sequence are shown in the single column along the right side of the figure. Again, darker values indicate higher adjusted binding affinity values. Each cluster of the dendrogram, at left, represents a different binding profile clustered via a correlation distance metric and agglomerative hierarchical clustering.
Figure 10:
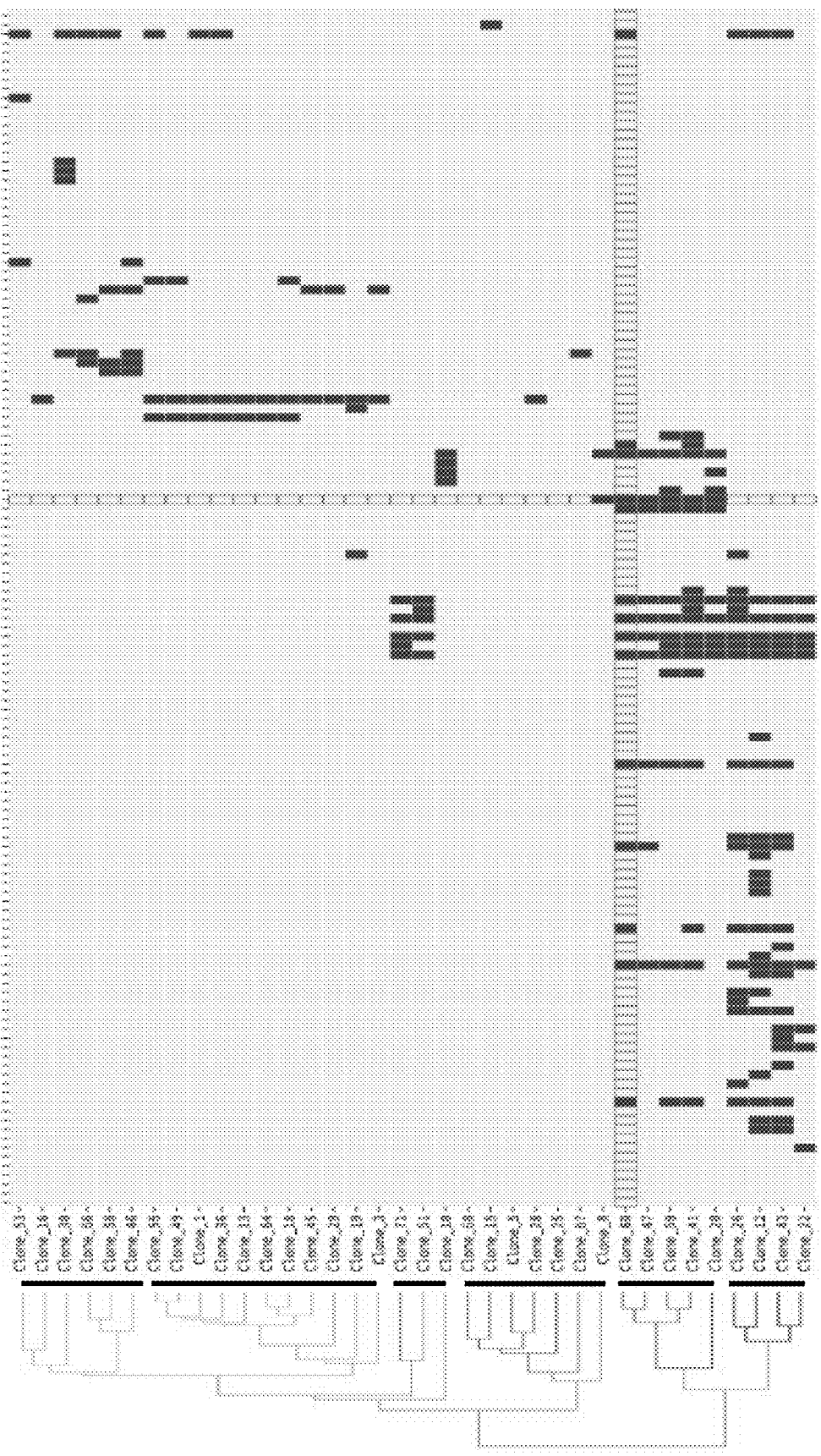
FIG. 10 is a heatmap of results from an epitope mapping experiment using hierarchical clustering results for the tumor necrosis factor receptor type II (TNFR2). Each column of the heatmap is a mutated site in the protein and each row is a binding site candidate. Darker regions of the heatmap indicate higher adjusted binding affinity values (higher $K_d$). These regions indicate putative binding sites. Each cluster of the dendrogram, at left, represents a different binding profile clustered via a correlation distance metric and agglomerative hierarchical clustering.

According to the methods described above, the TIGIT antigen sequence was comprehensively mutated into an SSM library comprising 1,469 individual mutations across 97 sites of the polypeptide. After filtering, 119 antibody candidates were clustered into five discrete epitope profiles using hierarchical clustering (see, FIG. 8). FIG. 8 is a heatmap of results of the results of this experiment. Each column of the heatmap is a mutated site in the SSM and each row is an antibody candidate. Darker regions of the heatmap indicate higher adjusted binding affinity values (higher $K_d$). These regions indicate putative epitopes. Adjusted binding affinities of each antibody to the wild-type antigen sequence are shown in the single column at the right side of the figure. Each of the five clusters of antibody candidates of the dendrogram, at left, represents a different epitope profile clustered via a correlation distance metric and agglomerative hierarchical clustering.

Individual mutations were grouped based on the combination of the wild-type amino acid at that site and the mutated amino acid into 328 feature groups. An 80/20 stratified train-test split of the data was performed with 100 different random states. After performing FFGS with KNN classification on each training set, an average of 16±23 groups were selected as the best core subset of feature groups with an average training accuracy of 99.81%±0.42%. The model retained a high average accuracy of 93.92%±4.90% on the test data. Ultimately, a total of 11 feature groups were selected in at least 25% of the iterations and made up the core feature set, including the mutation combinations GN, GY, AT, AI, AS, FI, FP. AL, AD, GL, and LH. The feature groups DV, EK, HP, IE, KE, MW, NL, PQ, QG, RK, SH, TR, VG, WN, and YA were added to the core subset to increase wild-type amino acid diversity, resulting in a total of 26 feature groups in the final subset composed of 108 individual mutations in the subset library.

These results indicate that the methods disclosed herein were able to reduce the number of feature groups in the TIGIT SSM library to 26 feature groups, reduced from an original 328 feature groups. According to these methods, reducing the SSM library size increases the number of antibody candidates that can be tested, thereby increasing throughput and proportionately reducing cost by over tenfold.

Example 2: Reducing a Library of SARS-COV2 RBD Variants

Using the same workflow as described in Example 1, the SARS-COV2 receptor-binding domain (RBD) antigen sequence was comprehensively mutated into an SSM library comprising 2,509 individual mutations across 165 sites. To filter the mutations, at this stage, only antibodies with measurable baseline binding to the target and for which binding was ablated by target mutations at one or more sites (i.e., antibodies for which determining epitope residues could be reasonably inferred) remain in the dataset for analysis. Only antibodies that had at least one site with ablated binding with a mean adjusted affinity greater than 1.9 were retained. The remaining 72 antibody candidates were hierarchically clustered into 7 epitope profiles (see, FIG. 9). FIG. 9 is a heatmap of results of the results of this experiment. Each column of the heatmap is a mutated site in the protein and each row is a binding site candidate. Darker regions of the heatmap indicate higher adjusted binding affinity values (higher $K_d$). These regions indicate putative binding sites. Adjusted binding affinities of each binder to the wild-type RBD sequence are shown in the single column at the right side of the figure. Each of the seven clusters of antibody candidates of the dendrogram, at left, represents a different epitope profile clustered via a correlation distance metric and agglomerative hierarchical clustering.

The antigen SSM library was reduced to contain only mutations belonging to the 26 feature groups identified from FFGS, resulting in a reduced library size of 178 individual mutations. The KNN model classified antibodies with 87.50% accuracy using the reduced SSM library.

Example 3: Reducing a Library of TNFR2 Variants

Using the same workflow as described in Example 1, the tumor necrosis factor receptor 2 (TNFR2) antigen sequence was comprehensively mutated into an SSM library comprising 3,525 individual mutations across 186 sites. This dataset required additional filtering to remove antibodies that showed no clear epitope profile, resulting in a remainder of 34 antibodies that clustered into six groups (see, FIG. 10). FIG. 10 is a heatmap of results from this experiment. Each column of the heatmap is a mutated site in the protein and each row is a binding site candidate. Darker regions of the heatmap indicate higher adjusted binding affinity values (higher $K_d$). These regions indicate putative binding sites. Each of the six clusters of the dendrogram, at left, represents a different binding profile clustered via a correlation distance metric and agglomerative hierarchical clustering.

The SSM library was subset to contain only mutations belonging to the 26 feature groups identified from FFGS, resulting in a reduced library size of 256 individual mutations. The KNN model classified antibodies with 61.76% accuracy using the reduced SSM library.

Example 4: Reducing a Second Library of TIGIT Variants

To assess the efficacy of the method to efficiently perform epitope binning (i.e., to identify from among a set of antibodies which antibodies target the same or similar epitopes), two libraries were created comprising variants of human TIGIT: one complete SSM library, and one reduced library utilizing the 26 amino acid substitutions listed in Table 1. These libraries were used in combination with a set of 52 novel anti-TIGIT antibodies derived from a phage panning campaign. These data were used to generate antibody- and residue-specific sensitivity scores indicating epitope engagement. Heatmaps and dendrograms showing clusters of the anti-TIGIT antibodies for the complete SSM library and the reduced library are shown in FIGS. 11 and 12, respectively.

Figure 11:
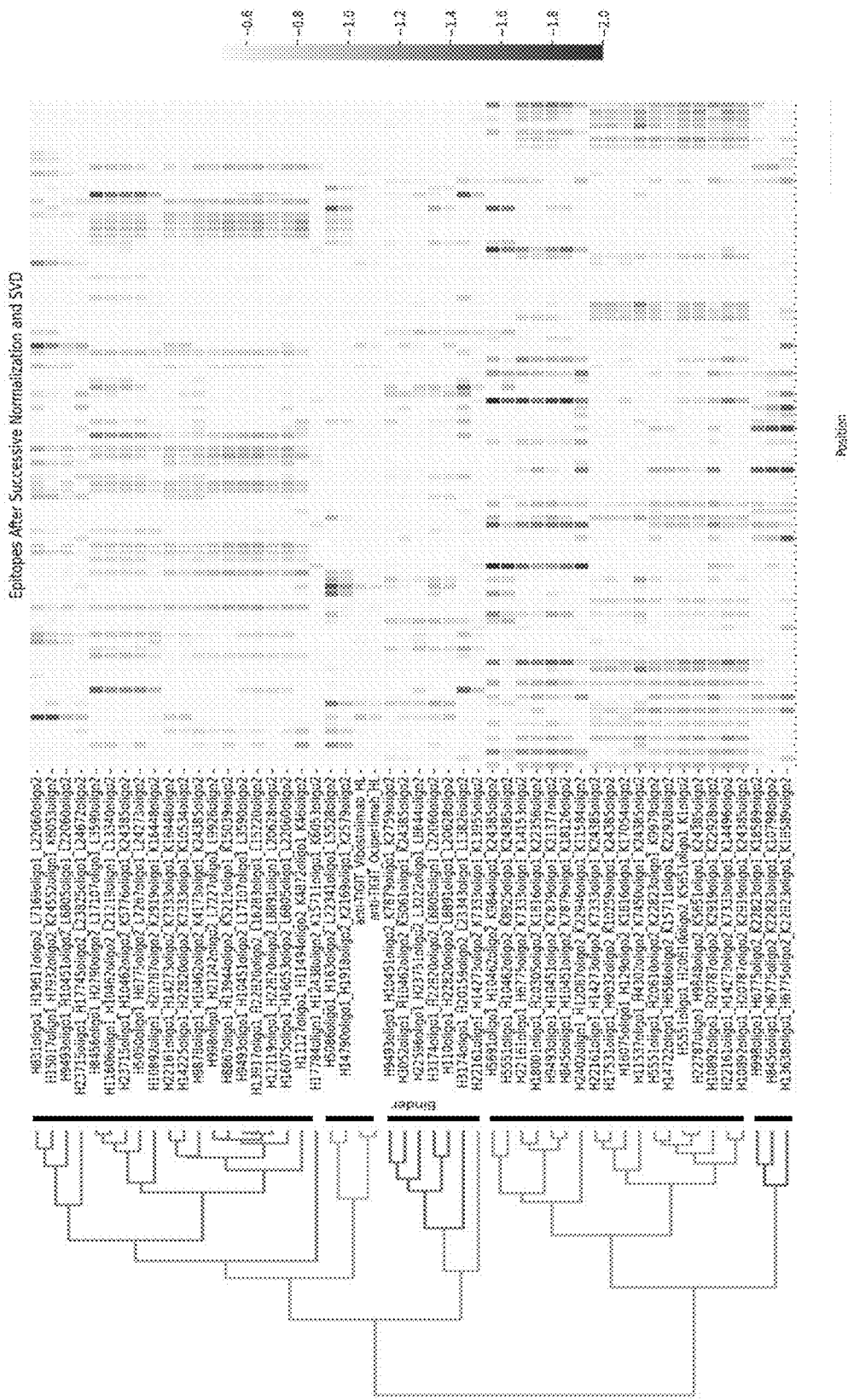
FIG. 11 is a heatmap of results from an epitope mapping experiment using hierarchical clustering results for the antigen target TIGIT using a full site-saturation mutagenesis (SSM) library. Each column of the heatmap is a mutated site in the SSM and each row is an antibody candidate. Darker regions of the heatmap indicate higher adjusted binding affinity values (higher $K_d$). These regions indicate putative epitopes. Each cluster of the dendrogram, at left, represents a different epitope profile clustered via a correlation distance metric and agglomerative hierarchical clustering.

FIG. 11 is a heatmap of results from this experiment using the complete SSM library. Each column of the heatmap is a mutated site in the SSM and each row is an antibody candidate. Darker regions of the heatmap indicate higher adjusted binding affinity values (higher $K_d$). These regions indicate putative epitopes. Each of the five clusters of the dendrogram, at left, represents a different epitope profile clustered via a correlation distance metric and agglomerative hierarchical clustering.

Figure 12:
FIG. 12 is a heatmap of results from an epitope mapping experiment using hierarchical clustering results for the antigen target TIGIT using a reduced library including the 26 amino acid substitutions listed in Table 1. Each column of the heatmap is a mutated site in the TIGIT target protein and each row is an antibody candidate. Darker regions of the heatmap indicate higher adjusted binding affinity values (higher $K_d$). These regions indicate putative epitopes. Darker values indicate higher adjusted binding affinity values. Each cluster of the dendrogram, at left, represents a different epitope profile clustered via a correlation distance metric and agglomerative hierarchical clustering.

FIG. 12 is a heatmap of results from this experiment using the reduced library including the 26 amino acid substitutions listed in Table 1. Each of the five clusters of the dendrogram, at left, represents a different epitope profile clustered via a correlation distance metric and agglomerative hierarchical clustering.

Antibodies with similar epitopes were defined as those with high binding affinity to TIGIT and a high pairwise correlation of residue sensitivity scores (e.g. row-wise correlation of the scores presented as heat-maps in FIGS. 11 and 12). Hierarchical clustering was performed, and the data were analyzed to assess the accuracy of epitope binning using the library with the reduced set of mutations. With respect to any particular numerical cutoff, the epitope bins defined by that cutoff are the sub-trees generated by using that cutoff as a maximum branch length after hierarchical clustering (e.g., equivalent to choosing a horizontal position on which to draw a vertical line through the dendrograms presented on the left of FIGS. 11 and 12).

Figure 13:
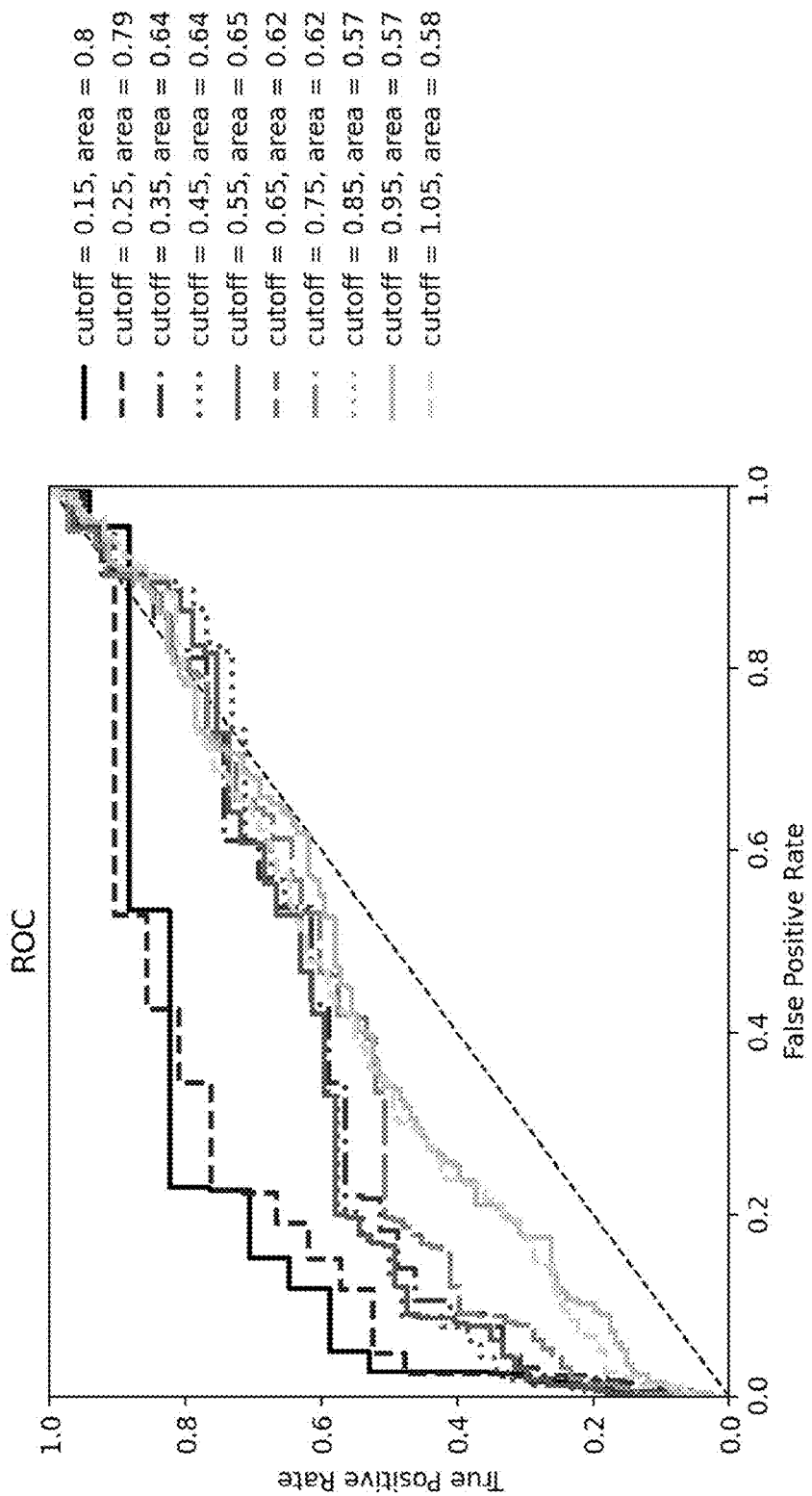
FIG. 13 is a graph of receiver operating characteristic (ROC) analysis performed at various experimental cutoffs for a library of TIGIT variants that was reduced according to the methods disclosed herein.

Finally, data from the full SSM experiment and data from the reduced library experiment were analyzed to determine accuracy for epitope binning. The specific metric investigated was, given a binning cutoff, the predictive power of pairwise correlation values from the experiment with the reduced library size to predict membership in an epitope bin in the experiment using the full SSM library. Receiver operating characteristic (ROC) analysis was performed, with a plot of these results shown in FIG. 13. Area under ROC curve (AUROC) of 0.5 would be expected to be achieved given random assignment of epitope bins, and AUROC of 1.0 would be expected to be achieved if reduced-library pairwise correlation values for all pairs of antibodies that share an epitope bin in the full SSM experiment were higher than all other pairwise correlation values. At the cutoff value of 0.25, an AUROC of 0.79 was achieved. The AUROC value of 0.79 at a cutoff of 0.25 demonstrates that in this Example, data generated using the reduced library of TIGIT variants using the 26 amino acid substitutions described in Table 1—approximately 7% the size of the full SSM library and therefore approximately 14-fold more efficient—is sufficient to recapitulate the epitope bins measured using the full-sized SSM library.

EXAMPLE 5: Implementing Methods in a Computing System

The methods disclosed herein were implemented by instructions written using the Python programming language running on a virtual machine provisioned by AWS EC2 (m5.12xlarge). The Python packages numpy and pandas were used for general data manipulation; hierarchical clustering was performed using the implementation in the scipy.cluster package. SciPy is an open-source software for mathematics, science, and engineering. SciPy packages for hierarchical clustering and for the correlation distance metric were used in these experiments. The sklearn package was utilized for KNN-classification and cross-validation algorithms. Forward feature group selection was performed as implemented in the eobox Python package. eobox is an open-source Python package including a collection of tools for machine learning applications.

Referring to FIGS. 14-27E, a script of instructions is presented that was executed to implement the method for reducing the size of the respective libraries for a library-by-library screen of protein-protein interactions (PPIs). As shown in FIG. 14, the required packages were loaded. As shown in FIG. 15, user-defined settings were selected, e.g., the script was run using settings for the TWIST TIGIT SSM library. As shown in FIGS. 16A-16B affinities per mutation type and per site were calculated. Affinities were adjusted by the wild-type affinity. Binders with a wild-type affinity greater than 3 were discarded.

As shown in FIG. 17, a colormap was normalized. As shown in FIGS. 18A-18B, binders were hierarchically clustered based on their adjusted affinities. Only rows where the maximum adjusted affinity value greater than 1.9 were retained. As shown in FIG. 19, flat clusters were formed from the hierarchical clustering defined by the given linkage matrix. As shown in FIGS. 20A-20B, features, targets, and values to feed into the forward feature group selection (FFGS) classification model were defined. Any sites that had greater than 90% adjusted affinities greater than 2 were removed. Codons that code fort eh same amino acid change were averaged. Only binders that clustered into groups by the clustering step of FIGS. 18A-18B were retained.

Feature names were designated (FIG. 21A), adjusted affinity values were designated (FIG. 21B), classification targets were designated (FIG. 21C), and an array of feature groups was established (FIG. 21D).

As shown in FIG. 22A, data were split into train and test sets. Different random states produced different results, accordingly, 100 random states were used to generate an average of best feature groups. As shown in FIG. 22B, data were split into train and test sets with different random states. Stratified sampling was used, and proportions of the dependent variable were kept similar in training and test sets.

Figures 26A, 26B, 26C:
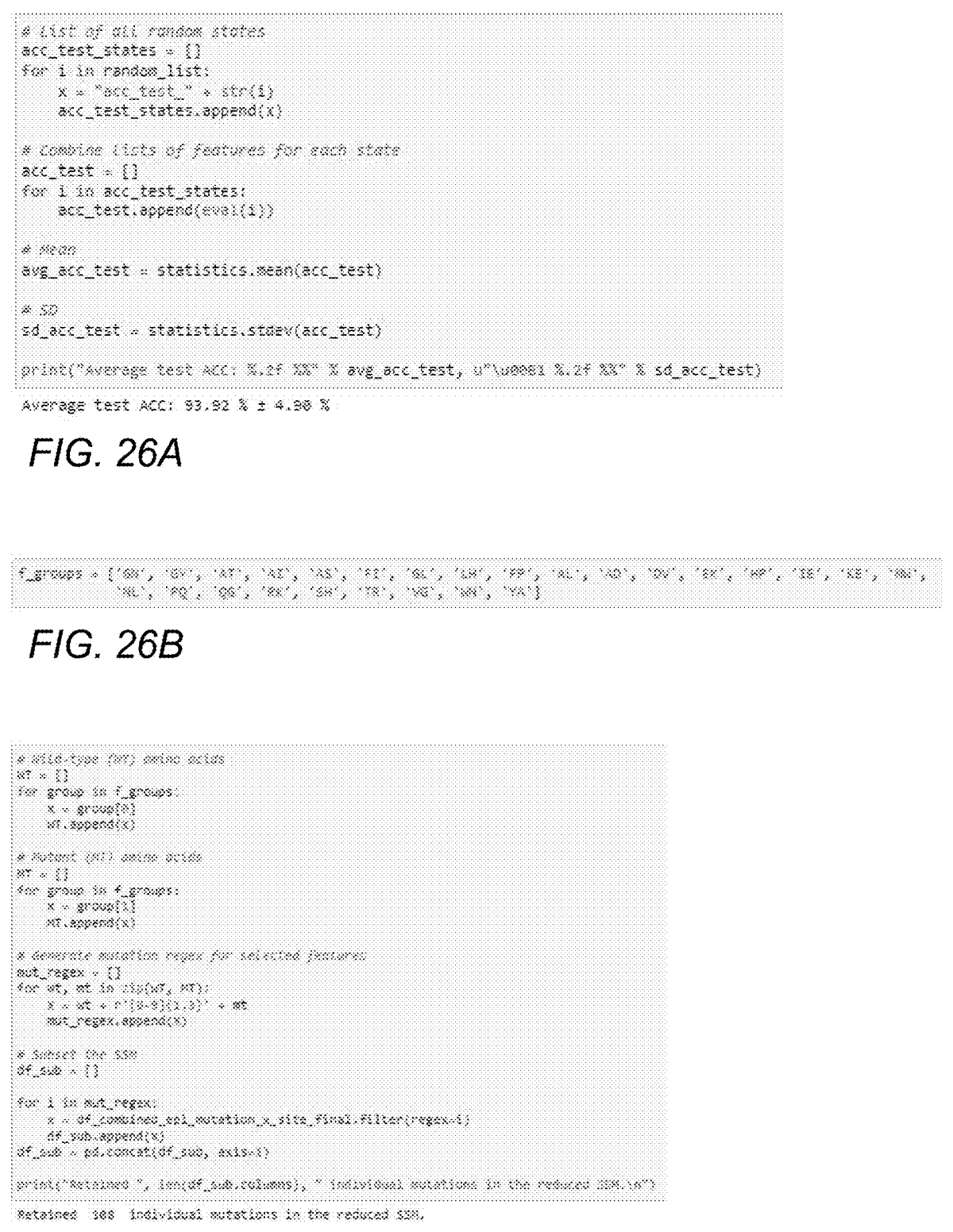

As shown in FIG. 23, a function to perform FFGS with K-nearest-neighbor (KNN) classification was defined. As shown in FIG. 24A, 100 iterations of FFGS with KKN classification were run. Each iteration had a different random state, and therefor split the train and test sets differently. As shown in FIG. 24B, the feature groups that were selected over 100 iterations were aggregated. As shown in FIG. 24C, the frequency of choosing each feature group over 100 iterations was plotted. As shown in FIG. 25A, the average number of feature groups selected over 100 iterations was calculated. As shown in FIG. 25B, the average training accuracy over 100 iterations was calculated. As shown in FIG. 26A, the average test accuracy over 100 iterations was calculated. As shown in FIG. 26B, the reduced set of feature groups was defined.

All feature groups were listed as the combination of the parental target protein amino acid residue and the mutant amino acid residue. For example, the "GN" feature group refers to all glycine to asparagine mutations across all sites. As shown in FIG. 26C, the full SSM library was subsetted to the reduced set of feature groups. Feature names were designated (FIG. 27A), adjusted affinity values were designated (FIG. 27B), classification targets were designated (FIG. 27C), and the classification model was applied to the subset SSM (FIG. 27D). Finally, 5-fold stratified k-fold cross-validation was performed (FIG. 27E).

The scripts of instructions and algorithms presented in this example can be adapted to any suitable programming language and executed on any suitable computing system to implement the methods for reducing the size of the respective libraries for a library-by-library screen of protein-protein interactions (PPIs), for any target protein and any binding polypeptides.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying amino acid substitutions that affect protein-protein interactions (PPIs), the method comprising:
providing a target library comprising a plurality of target polypeptide variants of a parental target protein;
measuring binding affinities between each target polypeptide variant of the target library and each of a plurality of binding polypeptides;
clustering, based on the binding affinities, the binding polypeptides to identify one or more groups of related binding profiles of the binding polypeptides;
applying a feature selection algorithm to the target library to identify a subset of target polypeptide variants of the parental target protein comprising amino acid substitutions that distinguish the one or more identified groups of related binding profiles from each other for binding to the target protein; and
providing a list of amino acid substitutions that affect PPIs from the subset of target polypeptide variants.

2. The method of claim 1, wherein the clustering is performed using a correlation distance metric.

3. The method of claim 1, wherein the clustering is performed using agglomerative hierarchical clustering.

4. The method of claim 1, wherein the feature selection algorithm is a forward feature group selection (FFGS) algorithm.

5. The method of claim 1, wherein the subset of target polypeptide variants is at least 2-fold smaller than the number of target polypeptide variants in the target library.

6. The method of claim 1, wherein the affinities are measured using yeast surface display of the target polypeptide variants and the binding polypeptides.

7. The method of claim 1, where the affinities are measured using synthetic yeast agglutination.

8. The method of claim 1, wherein the target polypeptide variants are antigens.

9. The method of claim 1, wherein the binding polypeptides are antibodies.

10. The method of claim 1, wherein applying the FFGS algorithm comprises providing a plurality of feature groups, wherein each feature group comprises target polypeptide variants sharing the same wildtype-to-mutant amino acid residue substitution at each position of the parental protein amino acid residue.

11. A method of reducing mutation space of a protein-protein interaction (PPI) screening platform, the method comprising:
providing a target library comprising one or more target polypeptide variants of each of two or more different parental target proteins;
measuring binding affinities between each target polypeptide variant of each parental target protein and each of a plurality of binding polypeptides;
clustering, based on the binding affinities, the binding polypeptides using a correlation distance metric and agglomerative hierarchical clustering to identify one or more groups of related binding profiles of the binding polypeptides;
applying a feature selection algorithm to the target library to identify a subset of target polypeptide variants of the one or more target proteins comprising amino acid substitutions that distinguish the one or more groups of related binding profiles from each other for binding to the target protein; and
providing a list of amino acid substitutions that affect PPI, thereby reducing the mutation space of a PPI screening platform.

12. The method of claim 11, wherein the subset of target polypeptide variants of the one or more parental target proteins is at least 2-fold smaller than the number of target polypeptide variants in the target library.

13. The method of claim 11, wherein the feature selection algorithm is a forward feature group selection (FFGS) algorithm.

14. The method of claim 11, wherein the affinities are measured using yeast surface display of the target polypeptide variants and the binding polypeptides.

15. The method of claim 11, where the affinities are measured using synthetic yeast agglutination.

16. The method of claim 11, wherein the target polypeptide variants are antigens.

17. The method of claim 11, wherein the binding polypeptides are antibodies.

18. The method of claim 13, wherein applying the FFGS algorithm comprises providing a plurality of feature groups, wherein each feature group comprises target polypeptide variants sharing the same wild-type to mutant amino acid substitution.

* * * * *